(12) United States Patent
Hofstetter

(10) Patent No.: US 12,027,064 B2
(45) Date of Patent: *Jul. 2, 2024

(54) CAMERA NAVIGATION TRAINING SYSTEM

(71) Applicant: Applied Medical Resources Corporation, Rancho Santa Margarita, CA (US)

(72) Inventor: Gregory K. Hofstetter, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/903,453

(22) Filed: Sep. 6, 2022

(65) Prior Publication Data

US 2023/0009004 A1 Jan. 12, 2023

Related U.S. Application Data

(63) Continuation of application No. 16/597,213, filed on Oct. 9, 2019, now Pat. No. 11,436,944, which is a
(Continued)

(51) Int. Cl.
*G09B 23/28* (2006.01)
*A61B 1/00* (2006.01)
(Continued)

(52) U.S. Cl.
CPC ........ *G09B 23/285* (2013.01); *A61B 1/00043* (2013.01); *A61B 1/05* (2013.01);
(Continued)

(58) Field of Classification Search
None
See application file for complete search history.

(56) References Cited

U.S. PATENT DOCUMENTS

2006/0183095 A1 8/2006 Korndorffer, Jr. et al.
2012/0308977 A1 12/2012 Tortola

FOREIGN PATENT DOCUMENTS

WO WO 2016/191661 A1 12/2016

OTHER PUBLICATIONS

European Patent Office, Extended European Search Report for European PatentApplication No. 22202986.0, titled "Camera Navigation Training System," dated Feb. 20, 2023, 8 pgs.
(Continued)

*Primary Examiner* — Christopher Braniff
(74) *Attorney, Agent, or Firm* — Thomas Nguyen; Patrick Ikehara

(57) ABSTRACT

A system for training surgical camera navigation skills is provided. A plurality of two-dimensional targets is printed on an upper surface of a flat sheet. The sheet is transportable and placed onto a base of a box trainer that defines a simulated abdominal cavity between the base and a top. A scope is inserted through a port in the top and the targets are viewed on a live video feed displayed on a screen. A trainee can move the scope back and forth, roll, and angulate the scope about the port to view the targets on the sheet at different angles and distances. The trainee is instructed to follow a sequence of targets marked on the sheet and manipulate the scope to align consecutively each target with the edges of the screen in the sequence provided.

19 Claims, 32 Drawing Sheets

Related U.S. Application Data continuation of application No. PCT/US2018/032378, filed on May 11, 2018.

(60) Provisional application No. 62/505,011, filed on May 11, 2017.

(51) Int. Cl.
| | |
|---|---|
| *A61B 1/05* | (2006.01) |
| *A61B 1/313* | (2006.01) |
| *H04N 23/00* | (2023.01) |
| *H04N 23/50* | (2023.01) |

(52) U.S. Cl.
CPC ........... *A61B 1/3132* (2013.01); *H04N 23/00* (2023.01); *H04N 23/555* (2023.01)

(56) References Cited

OTHER PUBLICATIONS

European Patent Office, The International Search Report and Written Opinion for International Application No. PCT/US2018/032378, entitled "Camera Navigation Training System," dated Jul. 27, 2018, 13 pgs.
The International Bureau of WIPO, International Preliminary Report on Patentability for International Application No. PCT/US2018/032378, entitled "Camera Navigation Training System," dated Nov. 12, 2019, 8 pgs.

CAMERA NAVIGATION TRAINING SYSTEM

CROSS-REFERENCE TO RELATED APPLICATIONS

This application is a continuation of U.S. patent application Ser. No. 16/597,213 entitled "Camera Navigation Training System" filed Oct. 9, 2019 which is a continuation of International Patent Application No. PCT/US2018/032378 entitled "Camera Navigation Training System" filed May 11, 2018 which claims priority to and benefit of U.S. Provisional Patent Application Ser. No. 62/505,011 entitled "Camera Navigation Training System" filed on May 11, 2017 which is incorporated herein by reference in its entirety.

FIELD OF THE INVENTION

This application relates to the surgical training, and in particular, to devices and methods for training scope/camera navigation skills in a laparoscopic environment.

BACKGROUND OF THE INVENTION

A highly-skilled operation technique is required of surgeons, in general, and in particular, for performing laparoscopic surgical procedures. In laparoscopic surgery, several small incisions are made in the abdomen for the insertion of trocars or small cylindrical tubes approximately 5 to 10 millimeters in diameter through which surgical instruments and a laparoscope are placed into the abdominal cavity. The laparoscope illuminates the surgical field and sends a magnified image from inside the body to a video monitor giving the surgeon a close-up view of organs and tissues. The surgeon performs the operation by manipulating the surgical instruments placed through the trocars while watching the live video feed on a monitor transmitted via the laparoscope. Because the surgeon does not observe the organs and tissues directly with the naked eye, visual information is obtained by a two-dimensional image on a monitor instead of a three-dimensional observation. The loss of information when presenting a three-dimensional environment via a two-dimensional image is substantial. In particular, depth perception is reduced when viewing a two-dimensional image as a guide for manipulating instruments in three dimensions.

Furthermore, because the trocars are inserted through small incisions and rest against the abdominal wall, the manipulation of instruments/scopes is restricted by the abdominal wall which has a fulcrum effect on the instrument/scope. The fulcrum effect defines a point of angulation that constrains the instrument/scope to limited motion. Also, hand motion in one linear direction causes magnified tip motion in the opposite direction. Not only is the instrument/scope motion viewed on the screen in the opposite direction, but also, the magnified tip motion is dependent on the fraction of the instrument/scope length above the abdominal wall. This lever effect not only magnifies motion but also magnifies tool tip forces that are reflected to the user. Hence, the operation of an instrument as well as a laparoscope with a fulcrum requires intentional learning and is not intuitively obvious.

Also, surgical instruments and scopes are placed through ports having seals which induce a stick-slip friction caused by the reversal of tool directions. For example, stick-slip friction may arise from the reversal of tool directions when, for example, quickly changing from pulling to pushing on tissue. During such motion, rubber parts of the seals rub against the tool shaft causing friction or movement of the tool with the seal before the friction is overcome and the instrument slides relative to the seal. Stick-slip friction, or oil-canning, at the seal and instrument/laparoscope interface creates a non-linear force on the instrument and a jarred image on the display. Such jarring can be distracting and practice of varying the insertion depth of a laparoscope is required to prevent it.

Hand-eye coordination skills are necessary and must be practiced in order to correlate hand motion with tool tip motion especially via observation on a video monitor. Also, in laparoscopic surgery, tactile sensation through the tool is diminished because the surgeon cannot palpate the tissue directly with a hand. Because haptics are reduced and distorted, the surgeon must develop a set of core haptic skills that underlie proficient laparoscopic surgery. The acquisition of all of these skills is one of the main challenges in laparoscopic training and the present invention is aimed at improving systems and methods for laparoscopic skills training and technique performance.

Also, during laparoscopy, a camera operator manipulates the laparoscope. The field of view is controlled by someone other than the surgeon. Oftentimes, the camera operator is the least experienced person. A medical student or intern is often tasked with navigating the camera, and must quickly learn skills necessary for providing optimal visibility such as recognizing and centering the operative field, maintaining the correct horizontal axis, knowing when to zoom in or out, holding a steady image, and tracking instruments in motion. An experienced camera operator is often someone who knows the case well enough that they can predict the next moves of the surgeon. Camera/scope navigation is crucial to the proper execution of laparoscopic surgical procedures as well as an important part of laparoscopic skills training. The camera operator must make complex camera movements to follow the movements of the surgeon that is performing the operation and overcome the difficulties outlined above.

Although movements vary depending on the surgical procedure being performed, a simple and universal method of training and assessing camera navigation skills is sought. Some studies have started investigating the impact of poor camera navigation in a surgical case, predicting that suboptimal imaging can lead to surgeon frustration and inefficiency. The studies indicate that the flow of the operation can be seriously disrupted when the surgeon must stop operating due to the inability to see which can also increase time in the operating room.

Not only do new practitioners have to learn laparoscopic skills but also trained laparoscopic surgeons seek to polish old skills as well as to learn and practice new surgical techniques that are unique to newly introduced surgical procedures. While training can be acquired in the operating room, interest in devising faster and more efficient training methods, preferably outside the operating room, has increased. Surgeons that attain a reasonable level of skills outside the operating room are better prepared when they enter the operating room and, thereby, valuable operating room experience can thus be optimized, lowering the risk to patients and reducing costs. To acquaint surgeons with basic surgical skills outside the operating room, various simulators have been devised and tested. An example of a surgical simulator is the SIMSEI® laparoscopic trainer manufactured by Applied Medical Resources Corporation in California and described in U.S. Pat. No. 8,764,452 incorporated by reference herein in its entirety. The SIMSEI® is not a computer-generated virtual reality trainer but one that employs three-dimensional live or fake organs or training games inside a simulated abdominal cavity that is obscured from direct observation by the user. There is a need for a camera navigation exercise for learning and increasing camera navigation skills. Such an exercise tool would allow trainees to gain the skills necessary for providing the best visibility for the surgeon prior to entering the operating room with zero degree and angled laparoscopes. The present invention provides an exercise platform and system for developing necessary scope/camera navigation skills for use in a laparoscopic training environment such as a laparoscopic trainer.

SUMMARY OF THE INVENTION

According to one aspect of the invention, a device for surgical camera navigation training is provided. A typical surgical scope includes a sensor connected to a rectangular video display screen having a screen perimeter and an aspect ratio of width to height. The device includes an insert having a flat upper surface with a plurality of two-dimensional targets printed on the upper surface. Each target is a projection of a virtual rectangle having an aspect ratio equal to the aspect ratio of the screen providing the scope with an orientation for each target about a port point located above the insert in which the orientation brings the target into congruency with the screen perimeter. The plurality of targets has a sequence indicated to the user that guides a user to achieve the orientation for each target for camera navigation training.

According to another aspect of the invention, a system for training surgical camera navigation is provided. The system includes a planar insert having a plurality of two-dimensional, trapezoidal targets on a flat upper side of the insert. Each target includes an associated fiducial reference marker indicating the orientation of each target with respect to the insert. A sequence marker is provided on the upper face of the insert indicated a sequence of targets and each target includes at least one alignment marker for aligning the target with at least one fixed reference.

According to another aspect of the invention, a method for training surgical camera navigation is provided. The method includes the step providing a scope having a sensor with a longitudinal axis perpendicular to a sensor plane. The scope is operably connected to a video screen encompassed by a rectangular frame having two oppositely disposed parallel long sides interconnected by two oppositely disposed parallel short sides defining an aspect ratio of long side to short side. The video screen is configured to display a live video feed from the scope. An insert is provided having a flat upper surface defining an X-Y plane. The insert includes a plurality of targets in the X-Y plane. Each target is a projection of at least one side of a virtual rectangle located above the X-Y plane. The projection is onto the X-Y plane and along an optical axis extending from a distal end of the scope. The scope is manipulated by the user to bring the projection of the at least one side of the virtual rectangle into congruency with a corresponding side of the frame.

DETAILED DESCRIPTION OF THE INVENTION

Figure 1:
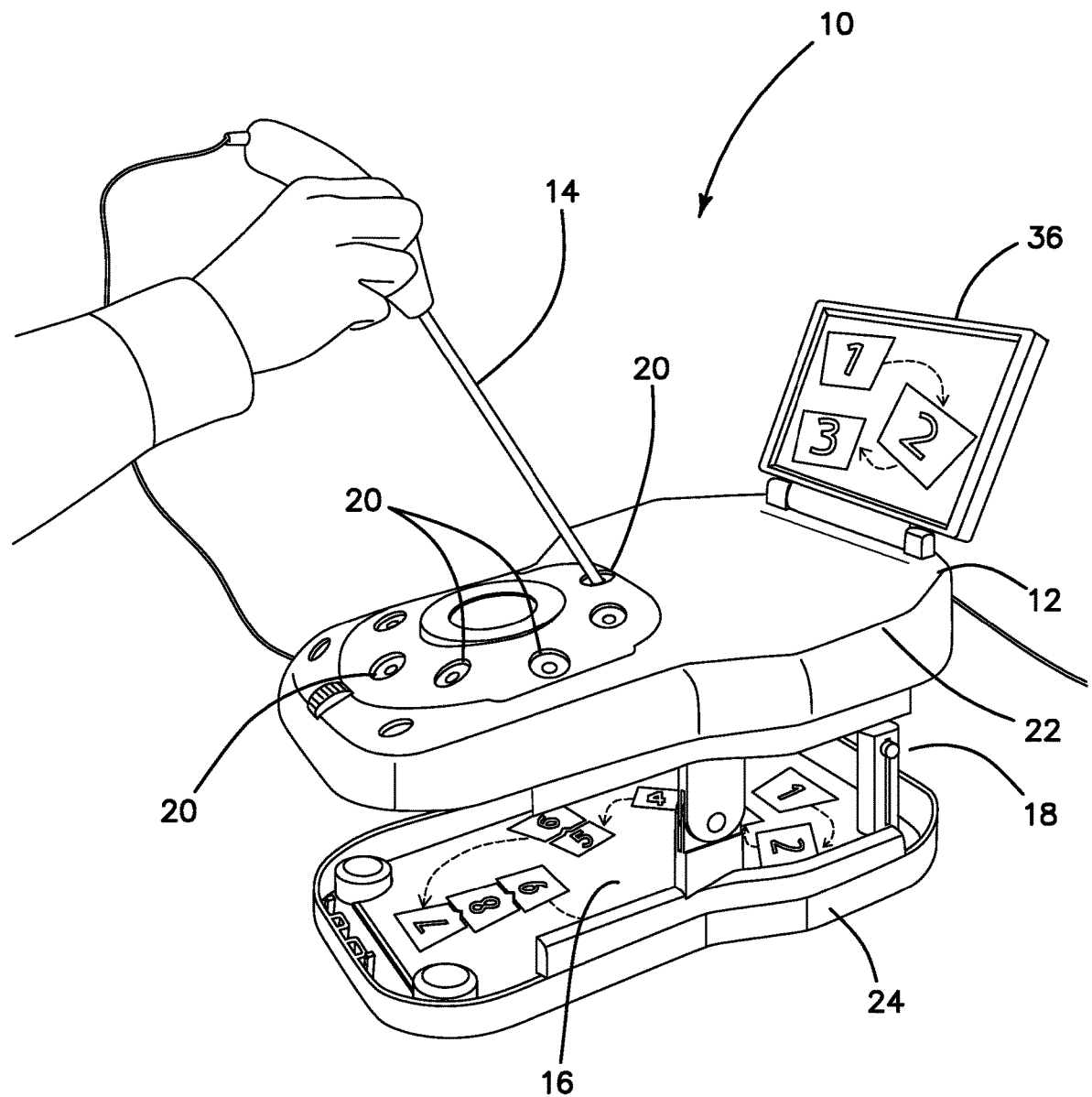
FIG. 1 is a top perspective view of a training system including a trainer and insert according to the present invention.

Turning now to FIG. 1, there is shown a camera navigation training system 10 according to the present invention. The system 10 includes a laparoscopic trainer 12, laparoscope 14 and an insert 16. The system 10 is an exercise designed for the practice and assessment of laparoscopic camera navigation skills using a 0-degree or angled laparoscope.

The laparoscopic trainer 12 allows a trainee to practice intricate surgical maneuvers in an environment that is safe and inexpensive. The trainer 12 is generally configured to mimic the torso of a patient, specifically the abdominal region. The surgical trainer 10 provides an enclosure for simulating a body cavity 18 that is substantially obscured from the user. The cavity 18 is sized and configured for receiving simulated or live tissue or model organs or training models as well as the insert 16 of the present invention. The body cavity 18 and the enclosed insert 16 are accessed with the scope 14 via one of the plurality of access ports 20 in order to view the insert 16 located inside the cavity 18. The surgical trainer 12 is particularly well suited for practicing laparoscopic camera navigation skills.

Still referencing FIG. 1, the surgical trainer 12 includes a top cover 22 connected to and spaced apart from a base 24. Sidewalls may be provided to completely cover and surround the cavity 18. The base 24 includes a frame that extends upwardly from the bottom surface inside the cavity 18. The frame is configured to receive a tray (not shown) or hold the insert 16 in position. An exemplary trainer 12 is the SIMSEI® laparoscopic trainer manufactured by Applied Medical Resources Corporation in California and described in U.S. Pat. No. 8,764,452 incorporated by reference herein in its entirety.

Figure 2:
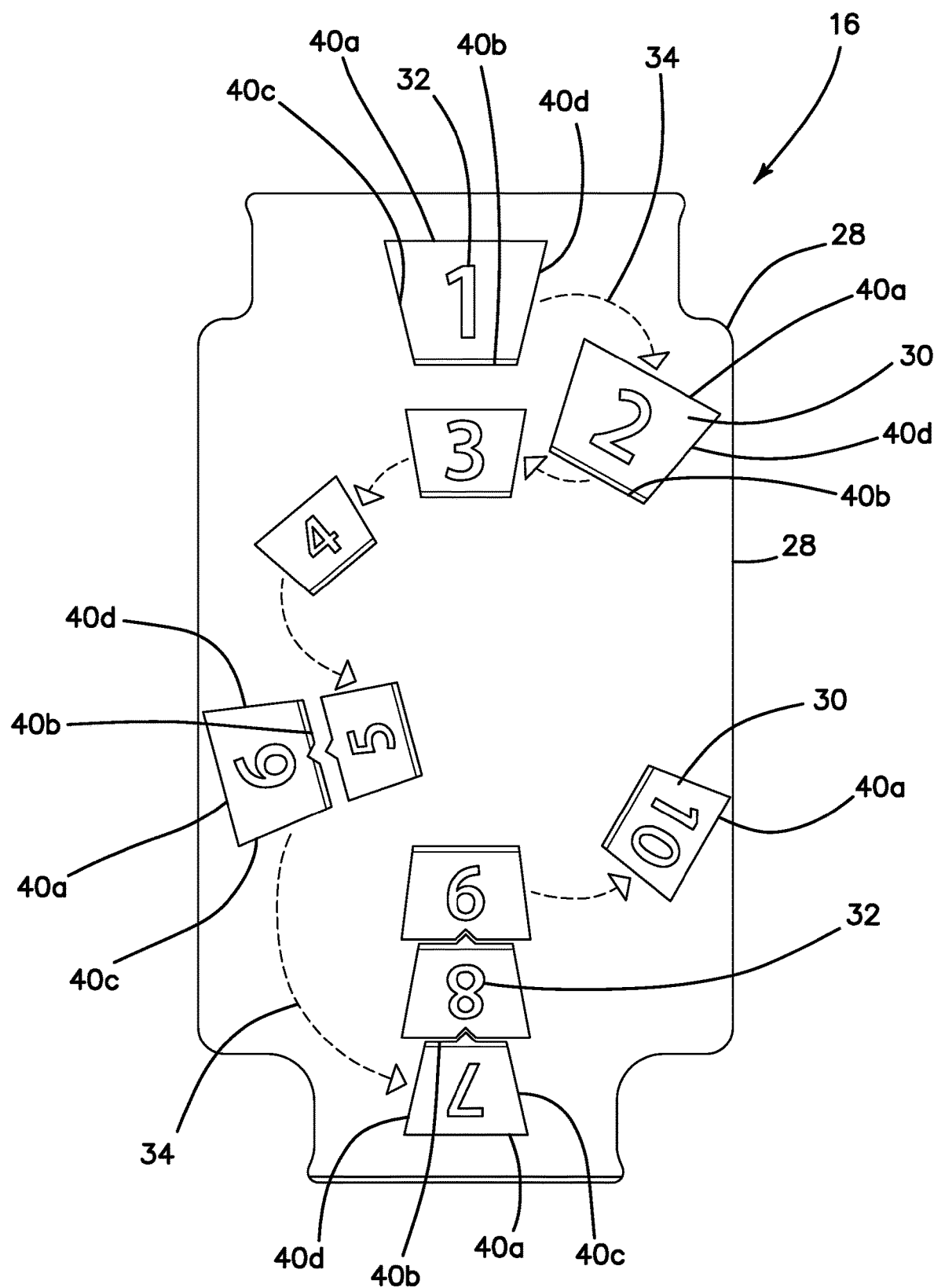
FIG. 2 is a top view of an insert according to the present invention.
Figure 3:
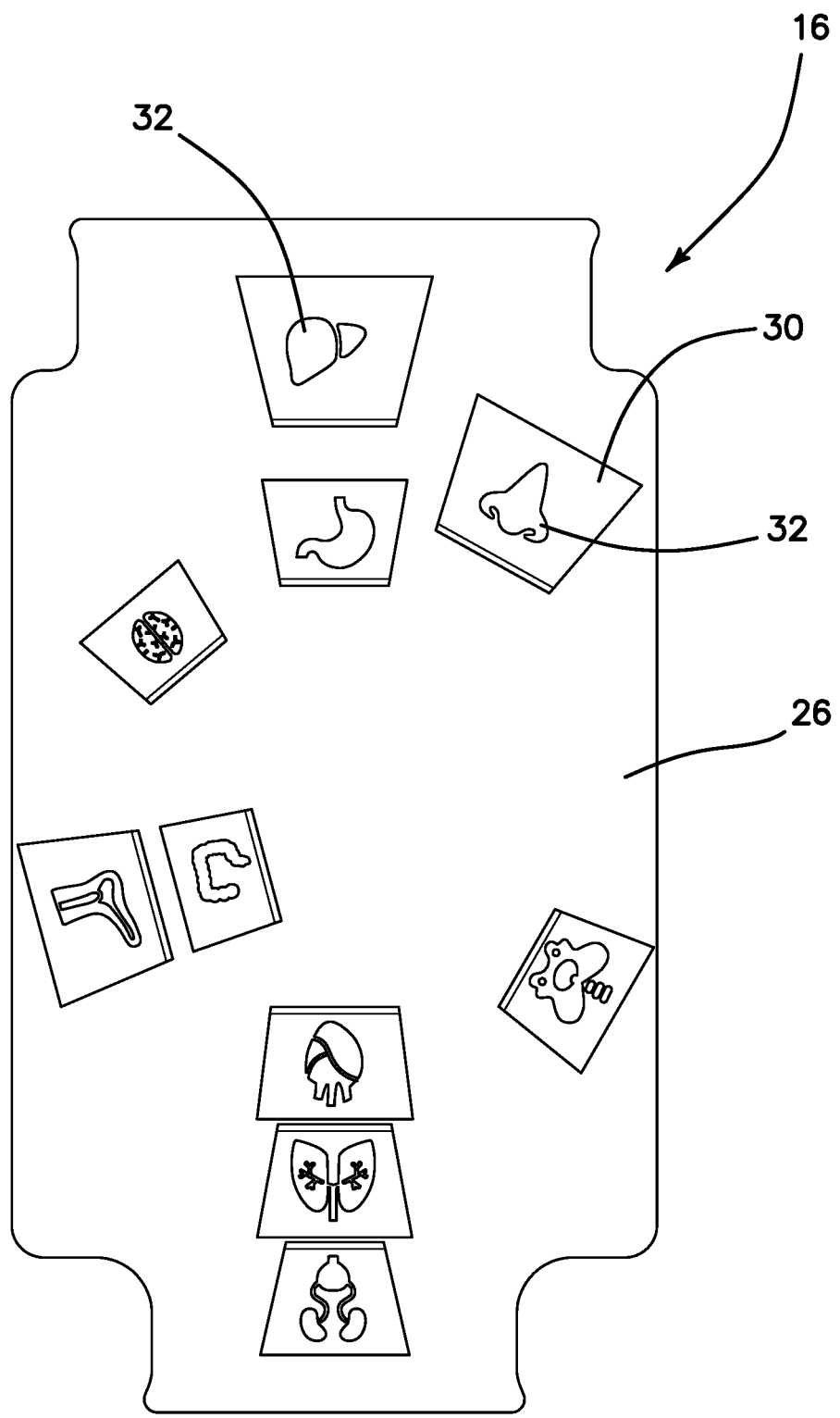
FIG. 3 is a top view of an insert according to the present invention.

Turning to FIG. 2 there is shown an exemplary insert 16 according to the present invention. The insert 16 includes a flat, planar top surface 26 and an oppositely disposed bottom surface 28. The insert 16 is sized and configured to be received in the frame of the base 24 of a trainer 12. The top surface 26 of the insert 16 includes a plurality of navigation targets 30. The targets 30 are shown to be quadrilateral and, in particular, trapezoidal; however, the invention is not so limited and the targets may be polygonal, or other shape as will be described in greater detail below. In one variation, each target 30 has at least one straight side or line interconnected by one or more curve or line. Each target 30 includes a marker 32 such as a number shown in FIG. 2. Each target 30 may also include a line at the bottom of the target 30 to denote which side of the target 30 is the bottom of the target 30 in order to alleviate confusion as to the proper orientation of the target 30. The top surface 26 may optionally further include a pathway 34 drawn on the top surface 26. The pathway 34 includes a line and arrow to indicate the sequence of targets 30 to the user. The marker 32 may be a word, letter, symbol or picture as shown in FIG. 3. The insert 16 of FIG. 3 may be used with a set of flashcards having a corresponding set of symbols or pictures as shown on the insert 16. The instructor may then draw a card from a plurality of cards and the user would then try to locate the symbol/picture on the insert 16 with the scope by bringing the symbol/picture into view on the display. The bottom surface 28 of the insert 16 may be provided with another pattern or arrangement of targets 30 that is different from the one on the upper surface 26 so that the insert 16 can be flipped over for a different arrangement of targets 30. In the variation in which each target 30 is a quadrilateral, each quadrilateral has a top side 40a, a bottom side 40b, a left side 40c and a right side 40d forming a trapezoid and, in particular, an isosceles trapezoid. The targets 30 are configured to be used with a particular scope/camera 14. The insert 16 is placed onto the base 24 of the trainer 12 as shown in FIG. 1. The sides of the insert 16 may include to cutouts to help position the insert 16 in the trainer 12.

Figure 4:
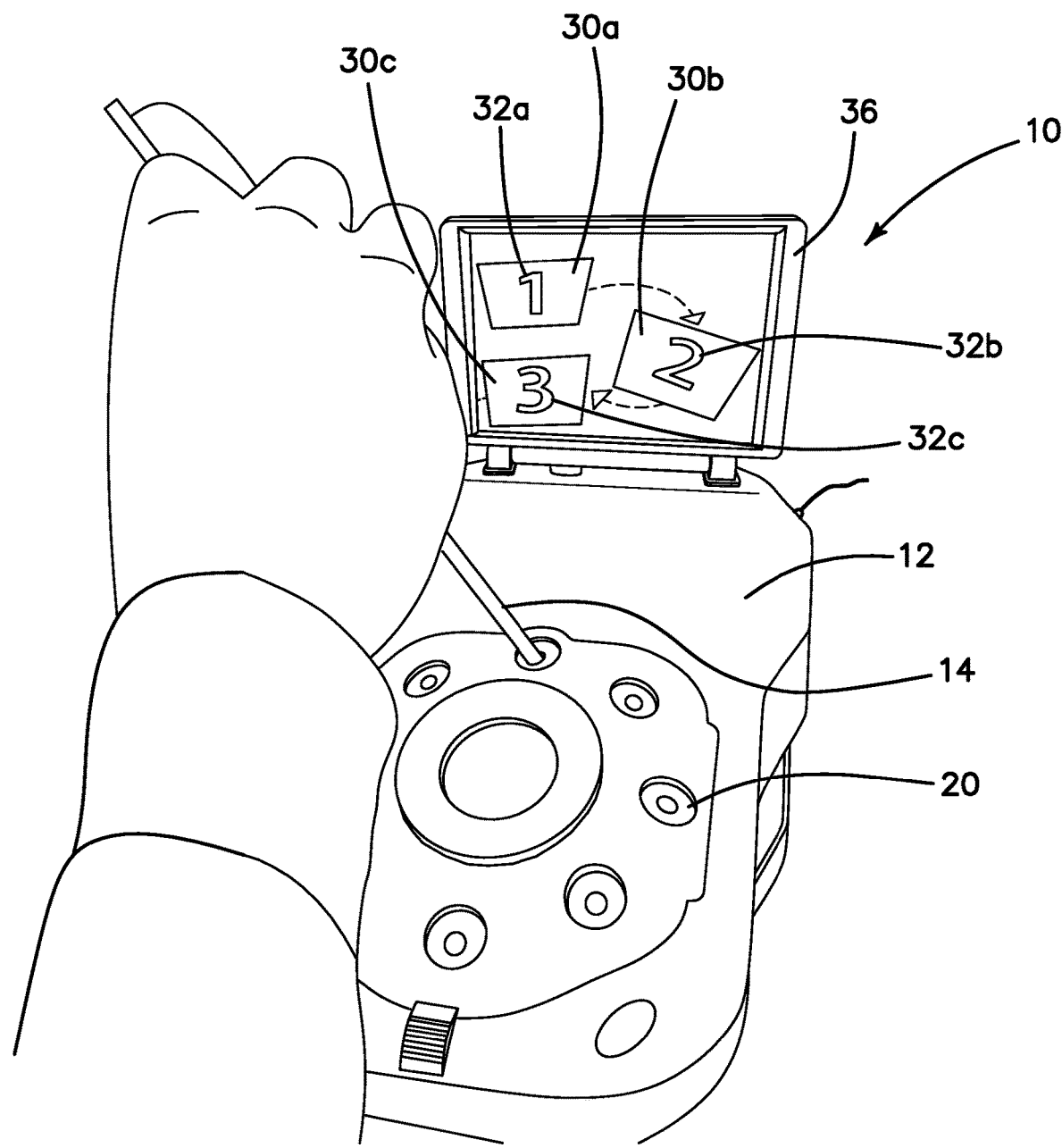
FIG. 4 is a top perspective view of a training system according to the present invention.
Figure 5:
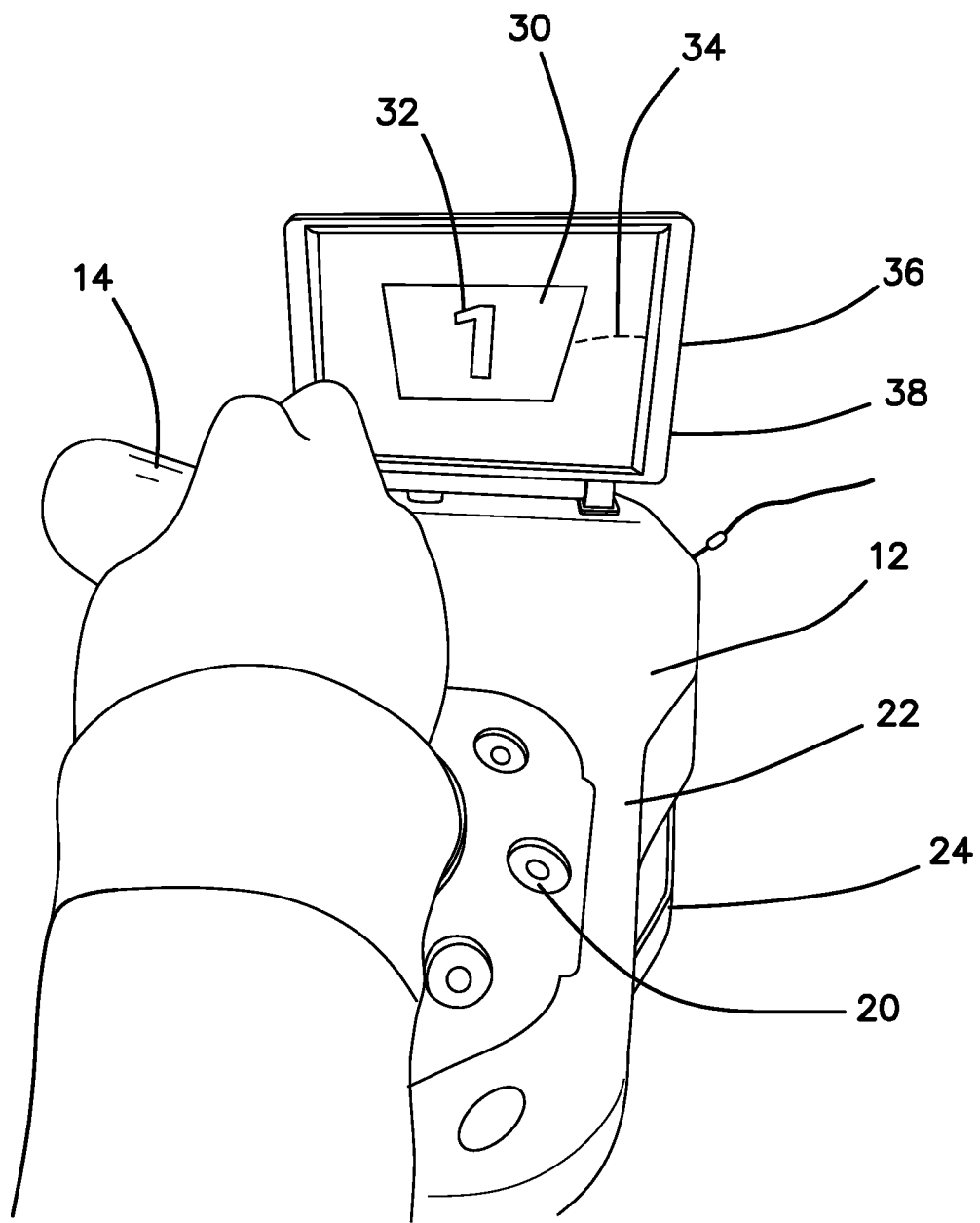
FIG. 5 is a top perspective view of a training system according to the present invention.
Figure 6:
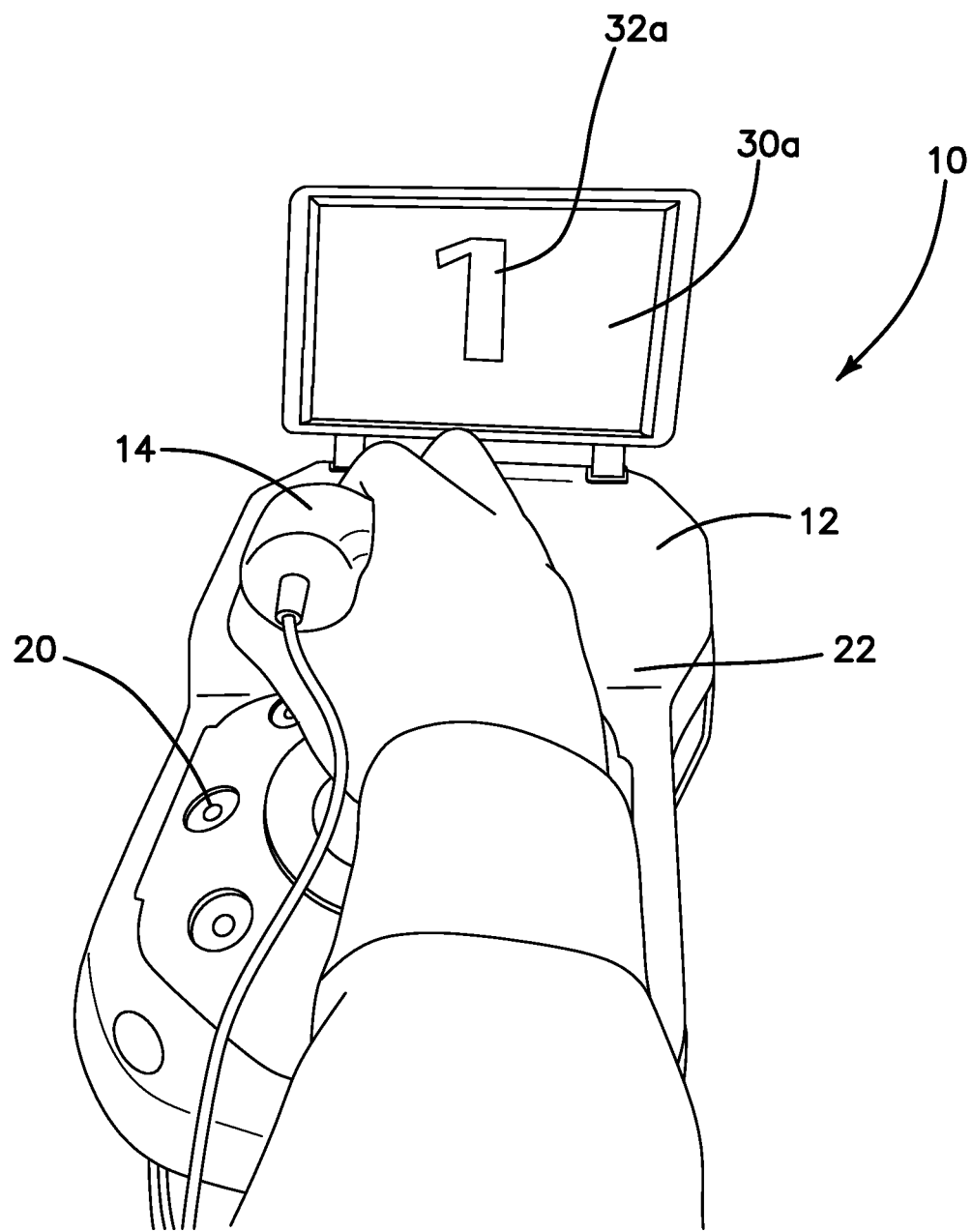
FIG. 6 is a top perspective view of a training system according to the present invention.

The scope 14 is configured to capture an image at its distal end and display the image on a video monitor 36 having a screen display 38 for the user to view the continuously captured live video image as the scope 14 is being manipulated in order to practice laparoscopic camera navigation. FIG. 4 illustrates the insert 16 of FIG. 2 inserted into the trainer 12 and placed flatly on the base 24 as shown in FIG. 1. The scope 14 is inserted into a port 20 and manipulated by hand. The display 38 shows the field of view captured by the scope 14 at any given time. As can be seen in FIG. 4, the top end of the insert 16 of FIG. 2 is shown displayed on the video monitor 36 with the first target 30a, second target 30b, and third target 30c visible on the display 38. The user is provided with a goal to sequentially bring into view the first target 30a followed by the second target 30b followed by the third target 30c and so on along a sequence if one is prescribed with a pathway 34, markers 32 or other means. In FIG. 4, the sequence of targets 30 is indicated to the user by the numeral markers 32a, 32b and 32c provided on each target 30. The goal for user is to not only to bring the targets 30 sequentially into view, but also, as an added level of difficulty, to bring each target 30 into view such that one target 30 fills the display 38 one target 32 at a time. Furthermore, the goal is increased in difficulty by requiring the scope 14 to be manipulated so as to bring the top side 40a of the target 30 parallel and/or congruent with the top side of the quadrilateral/rectangular display 38, the bottom side 40b of the quadrilateral/rectangular target 30 parallel and/or congruent with the bottom side of the quadrilateral/rectangular display 38, the left side 40c of the quadrilateral/ trapezoidal target 30 parallel and/or congruent with the left side of the quadrilateral/rectangular display 38, and/or the right side 40*d* of the quadrilateral target parallel and/or congruent with the right side of the quadrilateral display 38 such that the entire first target 30*a* fills the display 38 defining a "LOCK" position as shown in FIG. 6. If only one side, for example, is aligned then, the entire target may not fill the entire display 38 and this may certainly be a goal in one variation. If a target 30 has only one straight side, the rest of the target 30 is free to have any shape such as a curve and a successful "LOCK" would be defined by the one straight side being parallel and/or congruent with at least one side of the display 38. The side of the display 38 to be aligned with may be predefined by the user to achieve manipulation outcomes suitable for achieving training goals. Congruency may include coinciding and/or superimposing substantially all of the points of at least a portion of the perimeter, side or line of the target 30 with at least a portion the side of the display 38. In one variation, the entirety of the perimeter, line or side are coincided or superimposed on the one or more of the sides of the display 38. FIG. 5 is an intermediate position that requires the insertion depth of the scope 14 to be increased to bring the target 30 closer into view as shown in FIG. 6. The LOCK position is easily assessed visually by an assessor. To aid in the assessment, colored or color-contrast borders, lines or other may be provided.

Figure 7:
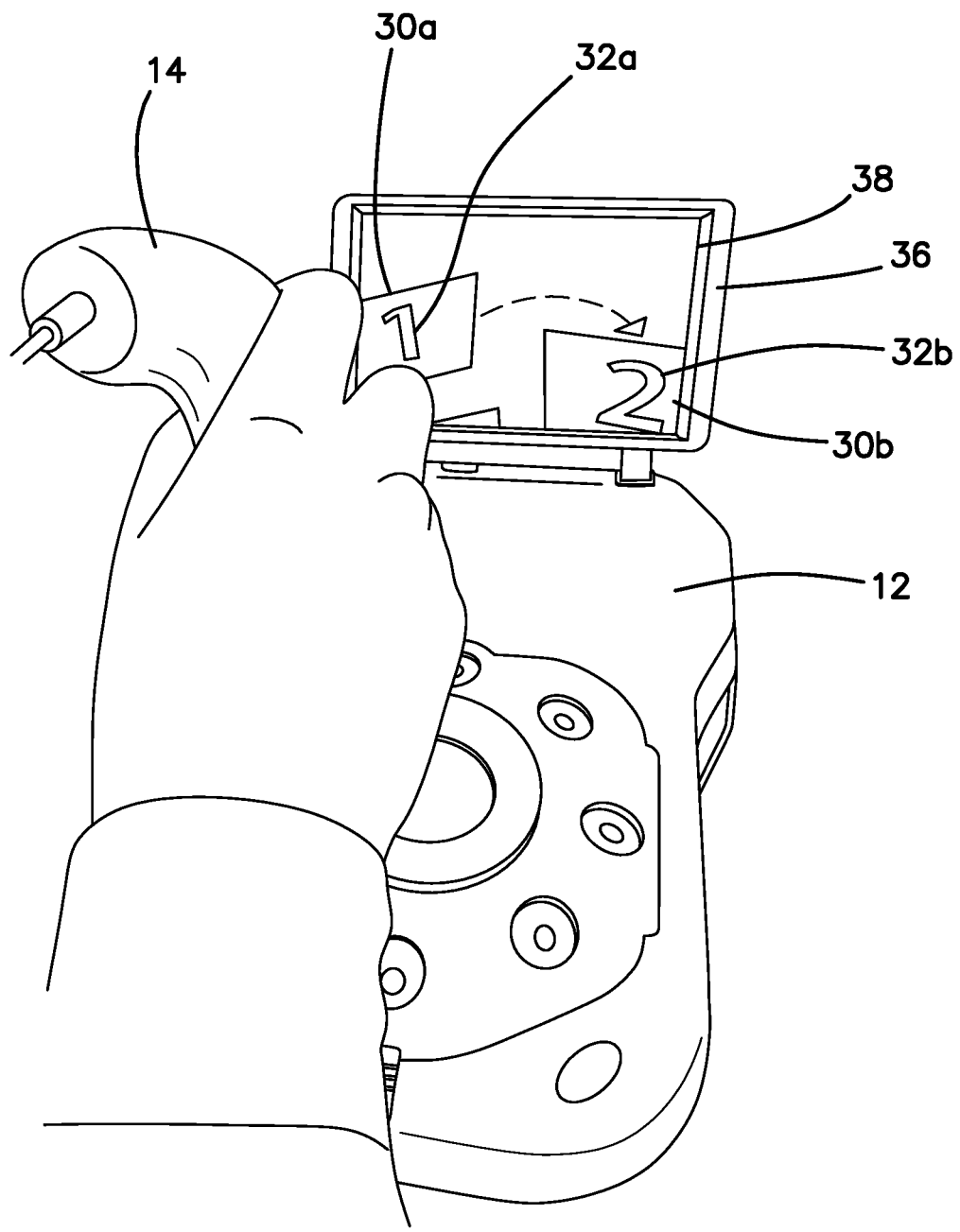
FIG. 7 is a top perspective view of a training system according to the present invention.
Figure 8:
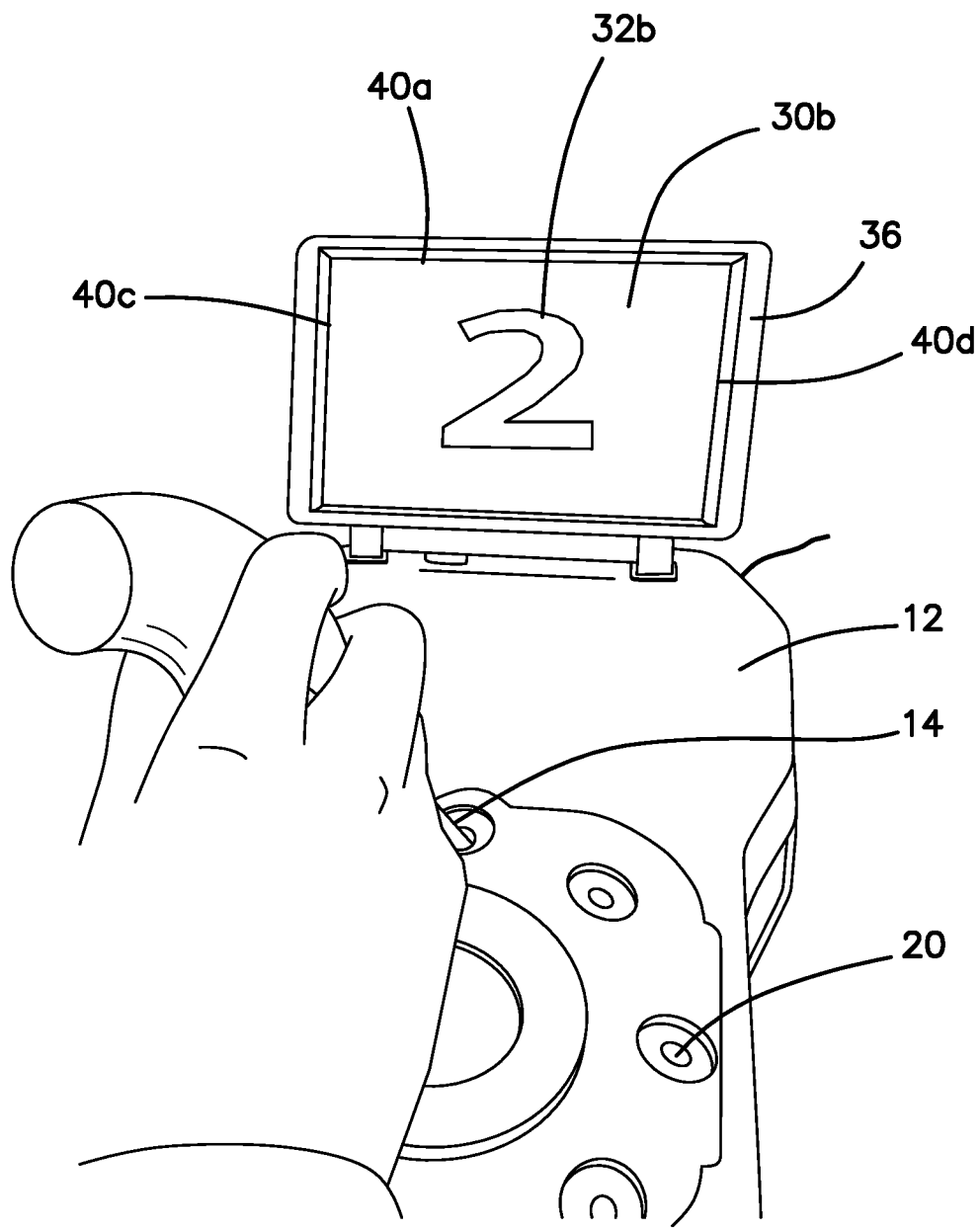
FIG. 8 is a top perspective view of a training system according to the present invention.

From the LOCK position, the user will then move the scope 14 to the next target 30. In the present example, the next target 30 is the second target 30*b* bearing numerical marker 32*b* which is number 2. The user can reduce the insertion depth of the scope 14 by pulling the scope 14 in the proximal direction to achieve a view on the display 38 as shown in FIG. 7 wherein the first target 30*a* and the second target 30*b* are within the frame defined by the display 38. A dotted arrow of the sequence pathway 34 is also visible in between the two targets 30*a*, 30*b*. The pathway 34 aids the user by providing a hint of the direction of the next target 30*b* as only part of the pathway 34 may be visible at any given time due to the limited field of view of the camera. The user moves the scope 14 to bring the second target 30*b* into a LOCK position as described above. FIG. 8 illustrates the second target 30*b* being slightly askew with respect to the top side 40*a*, left side 40*c* and right side 40*d* at the top end of the of the second target 30*b*. The user is urged by the exercise to manipulate the scope 14 to bring the second target 30*b* into a more perfect LOCK position or the assessor may deduct for lack of accuracy. The user will continue to seek each target 30 according to the sequence presented to the user by means of a marker 32 and/or pathway 34. In moving from the first target 30*a* to the second target 30*b* as shown in FIGS. 6-8, the user may have to rotate the scope 14 about its longitudinal axis and change the angle of the scope 14 shaft relative to the insertion port 20 of the top cover 22. Therefore, the two motions—rotate and angulate—are encoded in the arrangement of the first and second targets 30*a*, 30*b* relative to each other, which advantageously permits the system to teach a particular sequence of motions that may apply for a particular surgical procedure or combination of motions encountered in surgery or combination of motions that vary in difficulty for training purposes or to simply teach certain combinations of motions. The combination of one or more motions is, not only, encoded between two adjacent targets 30, but also, across multiple targets 30 or the entirety of the targets 30 on the insert 16.

Figure 9:
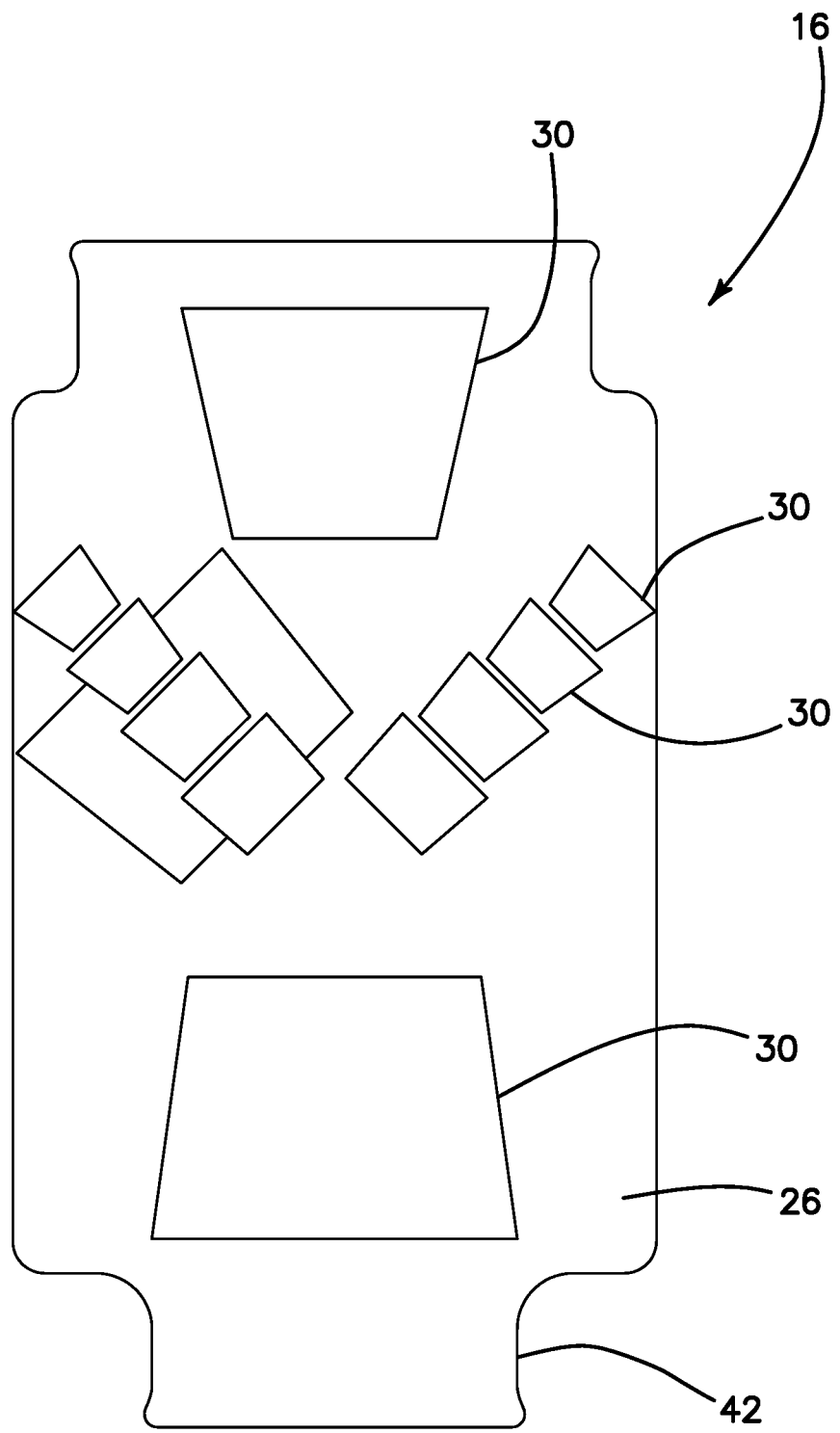
FIG. 9 is a top view of an insert according to the present invention.
Figure 10:
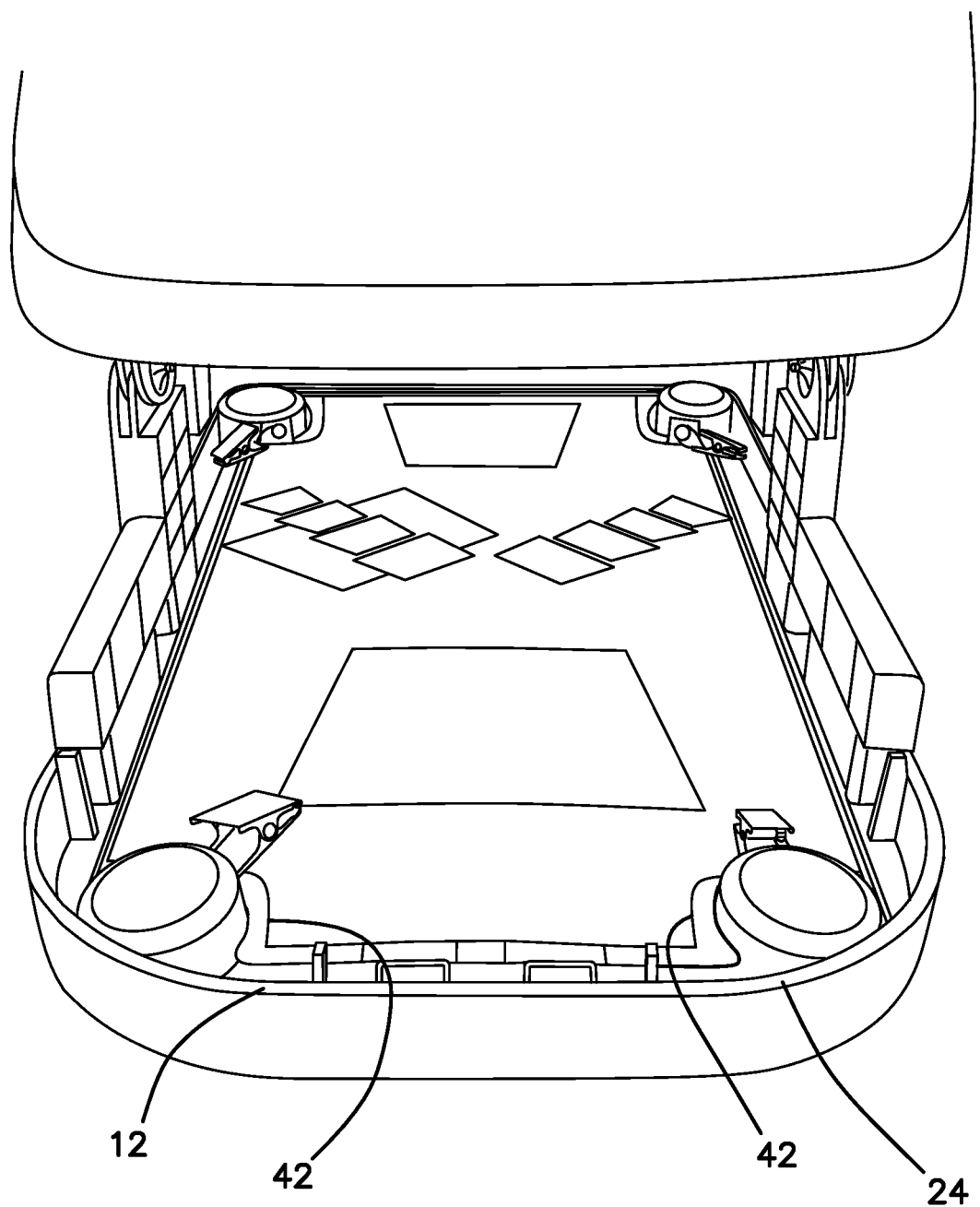
FIG. 10 is a top perspective view of an insert located in a base of a trainer according to the present invention.

For example, with particular reference to FIGS. 9-11, there is shown an insert 16 according to the present invention having an arrangement of a plurality of targets 30 printed on the top surface 26. In this variation, each target 20 has at least two opposite sides that are parallel and two opposite sides that are angled with respect to the other two sides. The insert 16 is shown laid flat on the base 24 of the trainer 12 in FIG. 10. The flat insert 16 may include contours and cutouts 42 so that the perimeter interfaces with the features found on the base 24 of the trainer 12 as can be seen in FIG. 10. The cutouts 42 and size of the insert 16 closely match the shape of the base 24 or a frame of the base 24 such that there is little or no room for the insert 16 to move with respect to the base 24. There is a single orientation of the insert 16 based upon the cutouts 42 that allows the insert 16 to sit flat on the base 24 of the trainer 12 and in this position, there is no room for the insert 16 to slide forward/backward or side-to-side. It is important to the functionality of the insert 16 with respect to the trainer 12 that the targets 30 are in a specific location with respect to a specific port 20 through which the scope 14 is inserted into the trainer 12. The scope 14 cannot be removed and inserted into another different port 20 on the trainer 12 and continue with the same insert 12 as an exercise in camera navigation as the target 30 geometries are set with respect to a particular port location relative to the trainer and insert. In essence, each insert 20 is customized to the location and distance of the insertion port 20 on the trainer that is to be used so that the optical geometry remains correct when aligning the targets 30 on the display 38. If the insert 16 is not in the correct location within the base 24 of the trainer, or the incorrect scope port 20 is used, the targets 30 will not align with the sides of the display 38 as intended for a LOCK position.

Figure 11B:
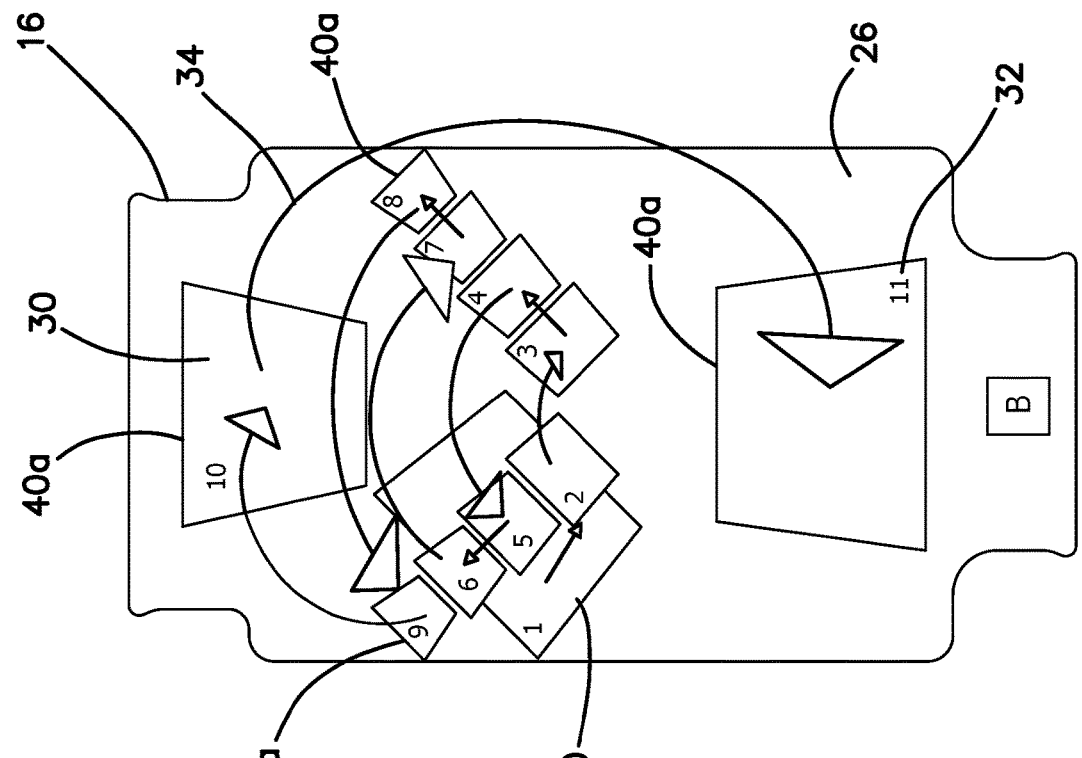
FIG. 11B is a top view of an insert according to the present invention.
Figure 11A:
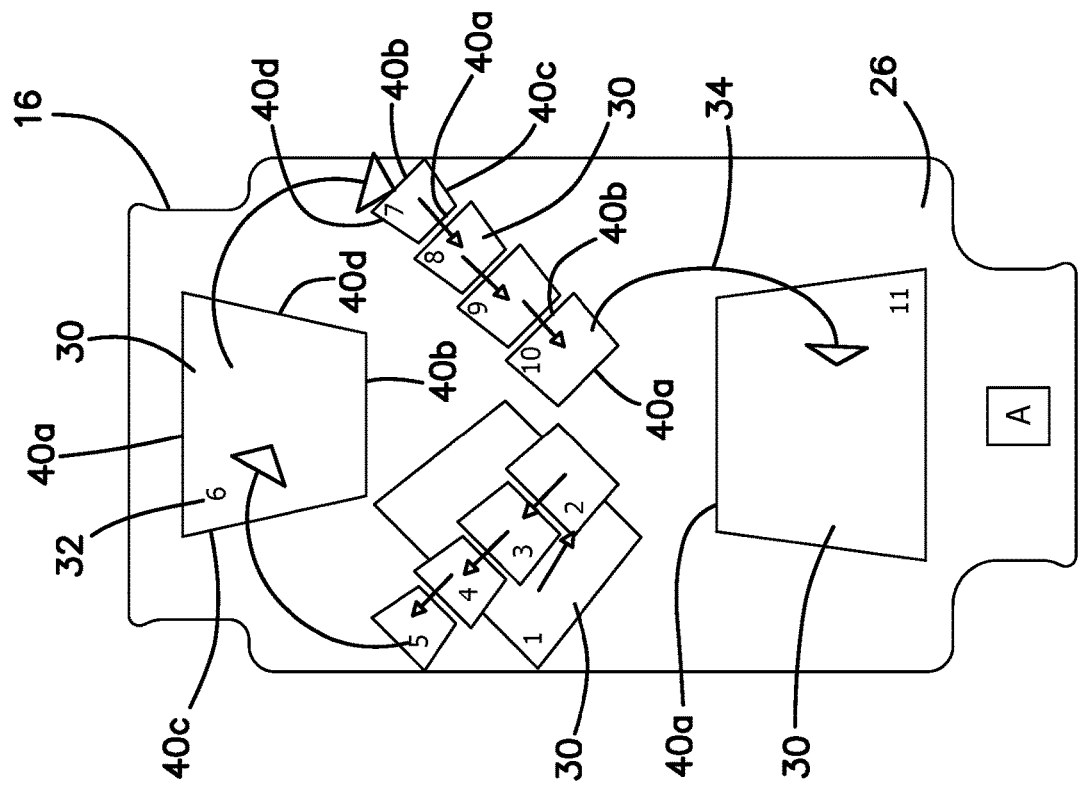
FIG. 11A is a top view of an insert according to the present invention.

FIG. 11A illustrates a first exemplary sequence of targets 30 defined by a markers 32 and a first pathway 34 indicated by a series of interconnected arrows. FIG. 11B illustrates a second sequence of targets defined by a second pathway 34 indicated by a series of arrows. The targets 30 are the same size and shape and in the same position in FIGS. 11A and 11B; however, by changing the sequence through which the user moves the scope indicated by numerical markers 32 numbered 1-11, the pathway 34 that the user follows as a goal pathway 34 in the exercise can be designed to be more or less difficult or to specifically train the user in a particular type of camera motion. Each movement between targets 30 can be designed with specific intent. For example, a move from one target to another may require only a change in camera insertion depth or any other of the parameters discussed hereinbelow or a move between targets may require a change in several or all possible camera position parameters. For example, in the first sequence shown in FIG. 11A, moving from target 6 to target 7 requires rotation of the scope 14 about its longitudinal axis and increasing the insertion depth; whereas, moving from target 6 to target 7 in FIG. 11B requires changing the polar angle. The size and position of the targets 30 combined with the sequence assigned to them defines a specific motion pathway. The targets 30 can be designed in such a way that they force the user to move the camera in a specific way that correlates to the camera movement for a specific surgical procedure or for a specific difficulty level. The sequence need not be defined to be in numerical organ and a random sequence of numbers may be called out to surprise the user and add an extra training dimension to the practice.

Figure 12:
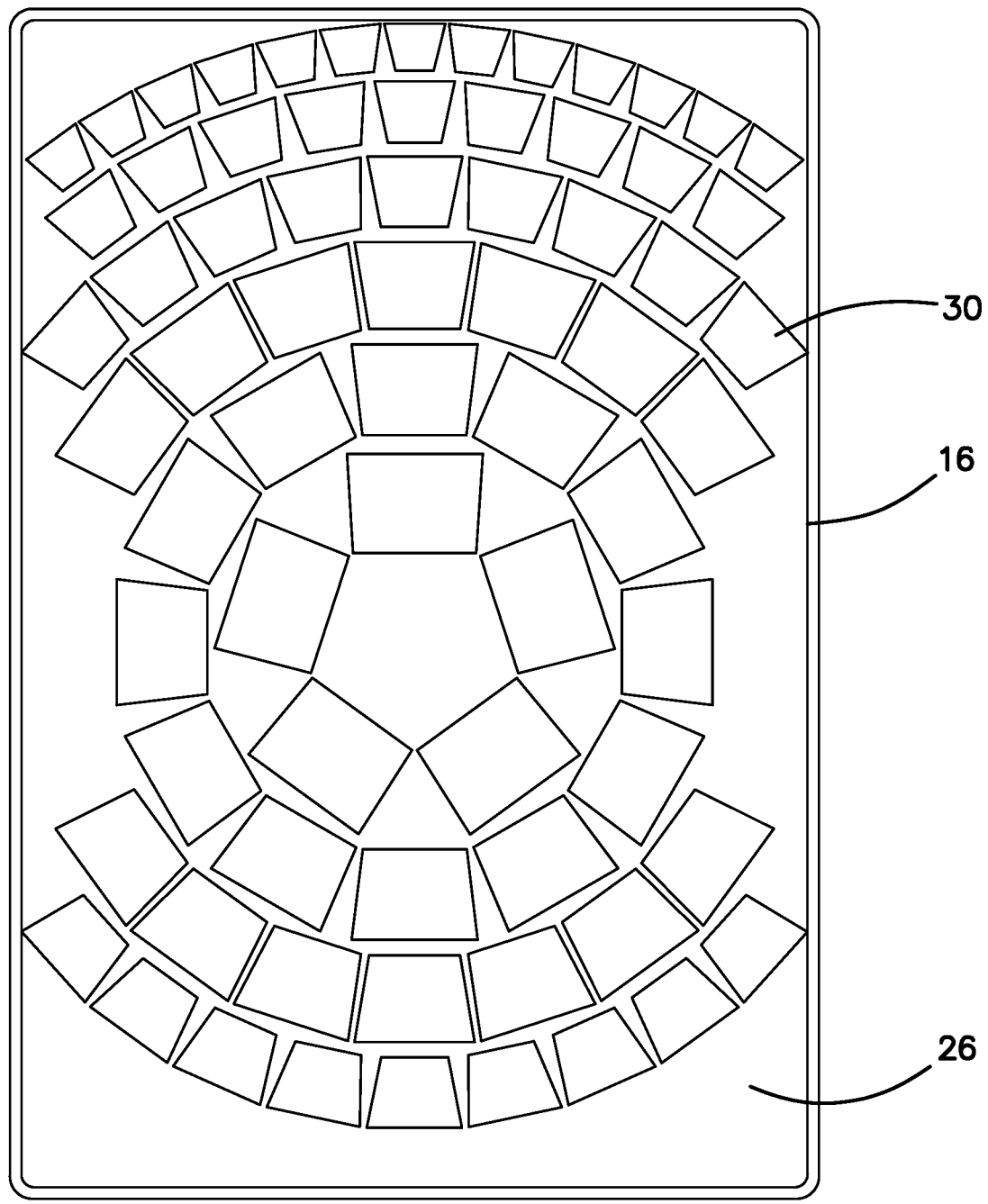
FIG. 12 is a top view of an insert according to the present invention.
Figure 13:
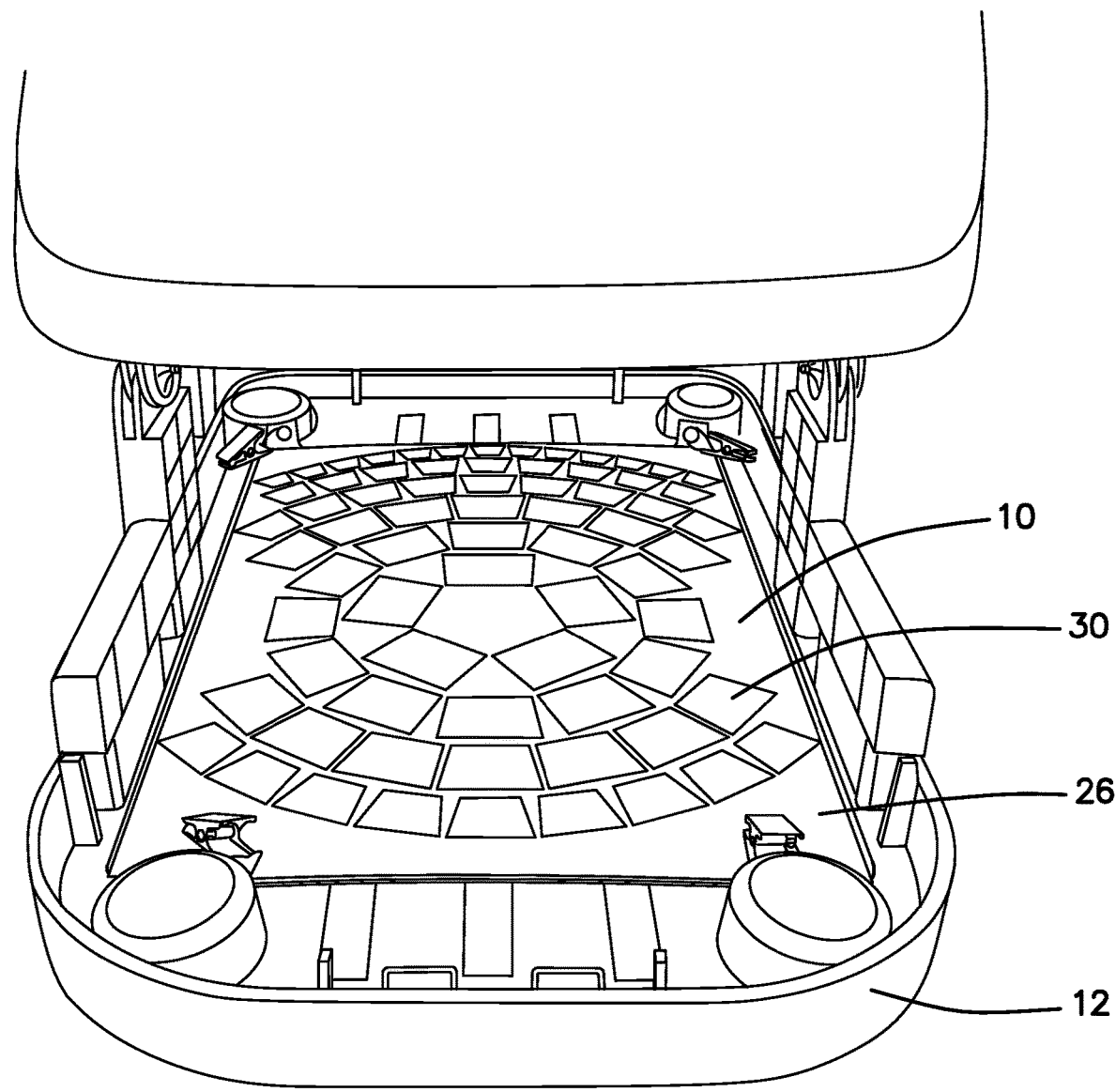
FIG. 13 is a top perspective view of an insert of FIG. 12 located in a base of a trainer according to the present invention.
Figure 14A:
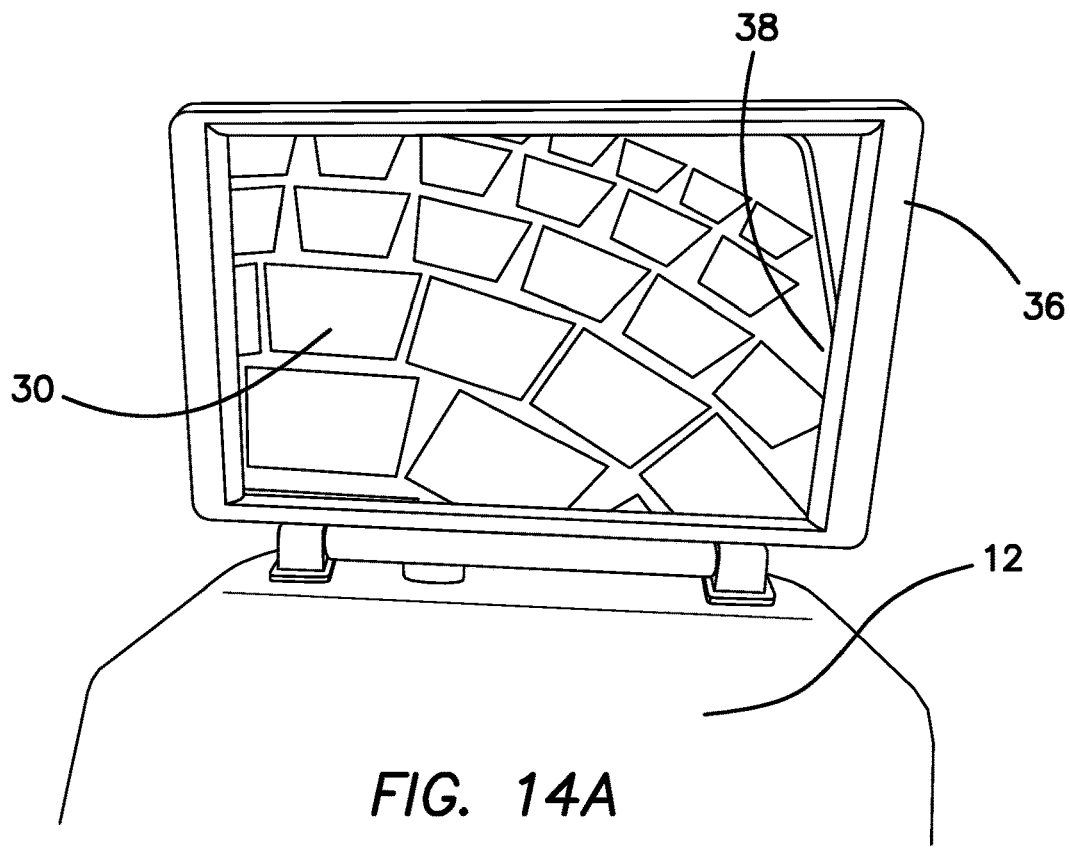
FIG. 14A is a top perspective view of a video monitor of a trainer displaying a portion of an insert according to the present invention.
Figure 14B:
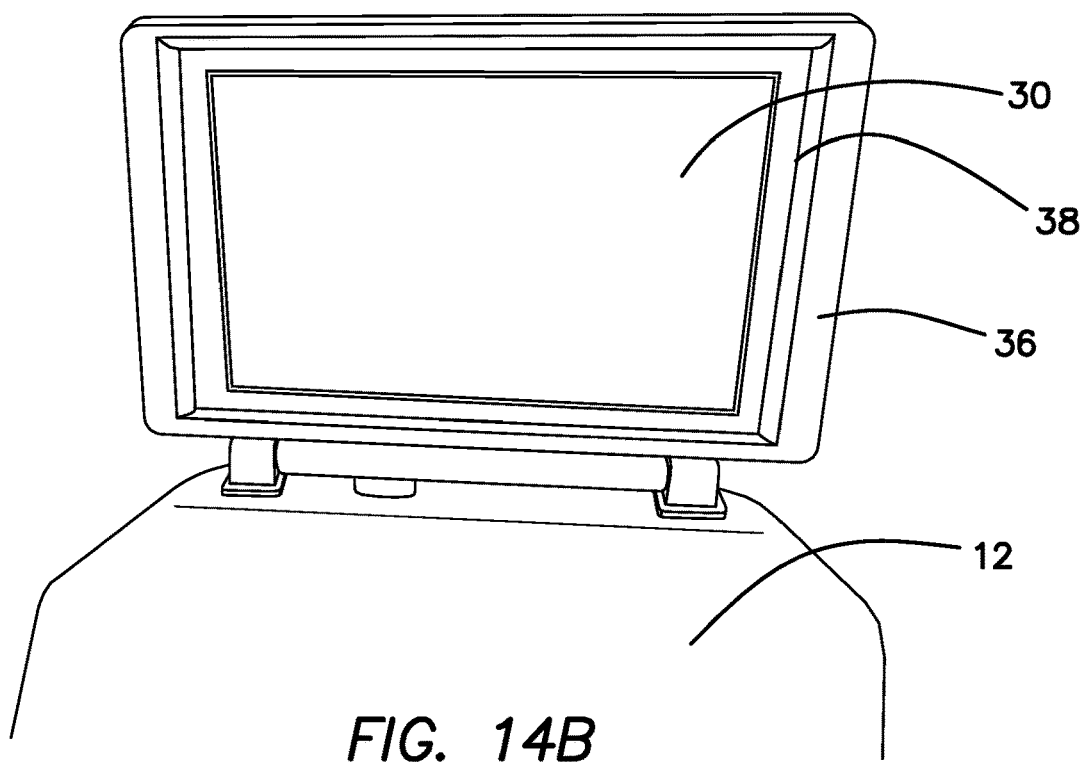
FIG. 14B is a top perspective view of a video monitor of a trainer displaying a target in a LOCK or HIT position with respect to the screen display according to the present invention.

Turning now to FIGS. 12-14, there is shown another insert 16 according to the present invention having a plurality of targets 30 printed on the top surface 26. In this variation, there are no markers 32, such as numbers/letters, to indicate a pathway 34 or sequence of targets 30 to follow. However, the insert 16 includes a transparent interchangeable layer having a pathway sequence of numbers or non-removable laminate layer attached to the top surface 26 that permits a dry-erase marker to be used to write markers 32 or draw a pathway 34 on the insert 16. The pathway 34 can be marked to simulate a specific surgical procedure. FIG. 13 illustrates the insert of FIG. 12 located inside the cavity 18 of a trainer 12. FIG. 14A illustrates a video monitor 36 with a display 38 showing the field of view captured by a scope 14 to include a portion of the plurality of targets 30 on the insert 16 of FIG. 12. FIG. 14B illustrates a LOCK position wherein one target 30 is fitting within the frame of the display 38 such that the sides of the target 30 nearly match the sides of the display 38 and are parallel therewith. All of the two-dimensional target geometries printed on the insert 30 will appear rectangular to match the rectangular shape of the screen when the scope is in the encoded position with respect to the insert/trainer. The geometries of the targets 30 are not rectangular but trapezoidal on the insert and on the screen until a LOCK position is achieved.

Figure 15:
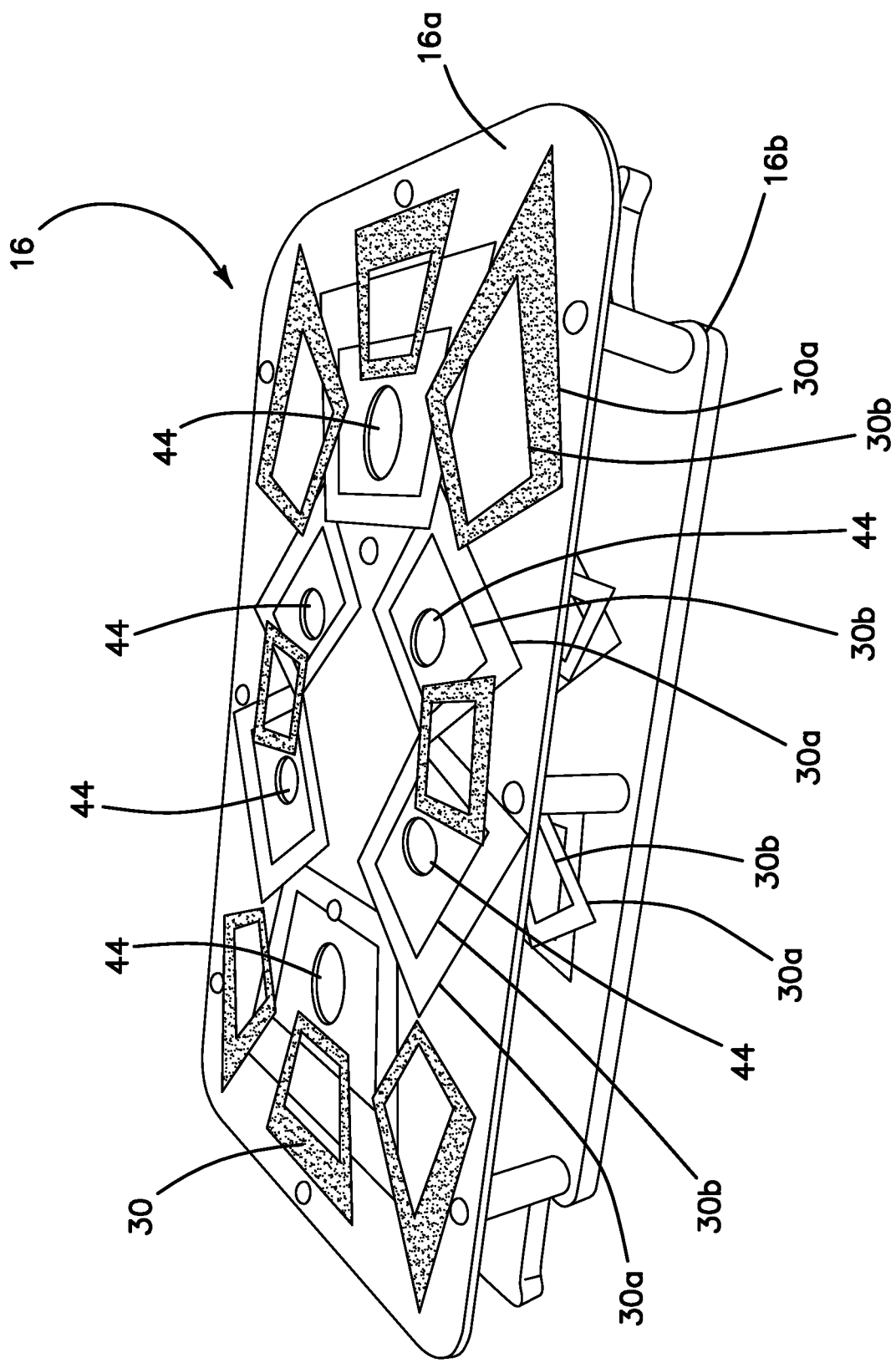
FIG. 15 is a top perspective view of an insert according to the present invention.
Figure 16:
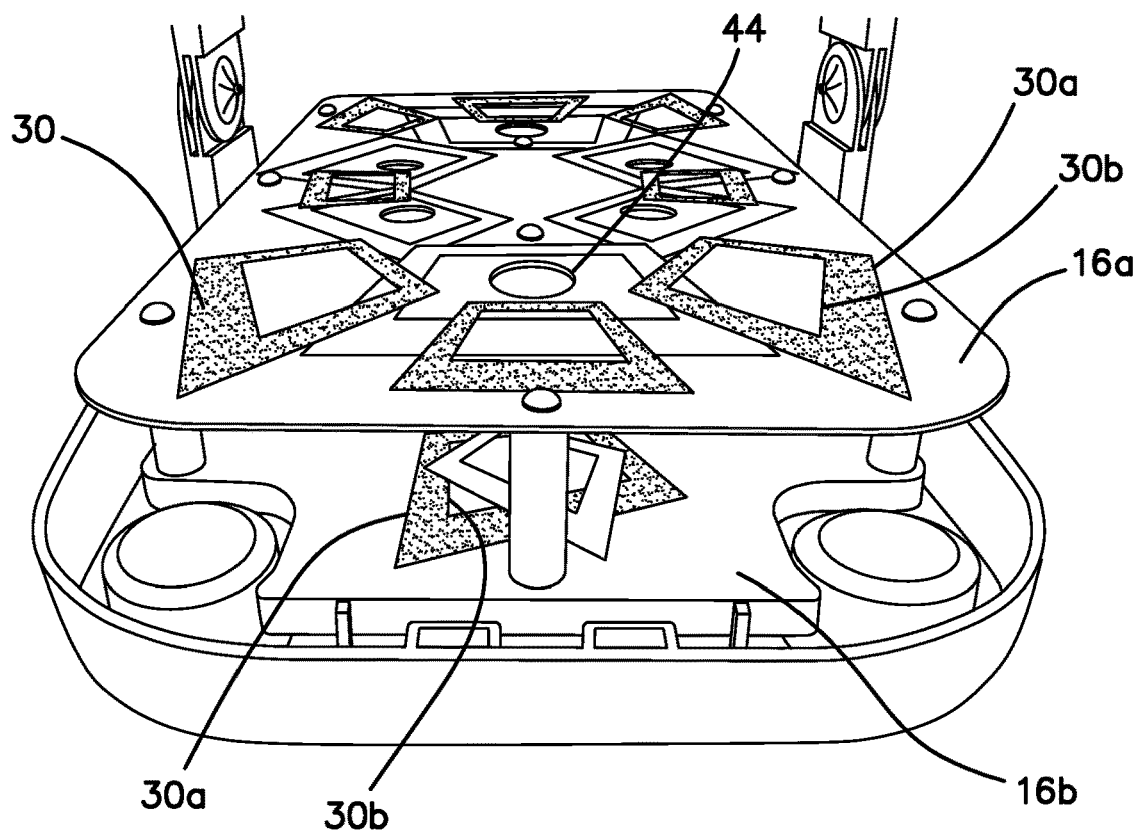
FIG. 16 is a top perspective view of an insert of FIG. 15 located on a base of a trainer according to the present invention.
Figure 17:
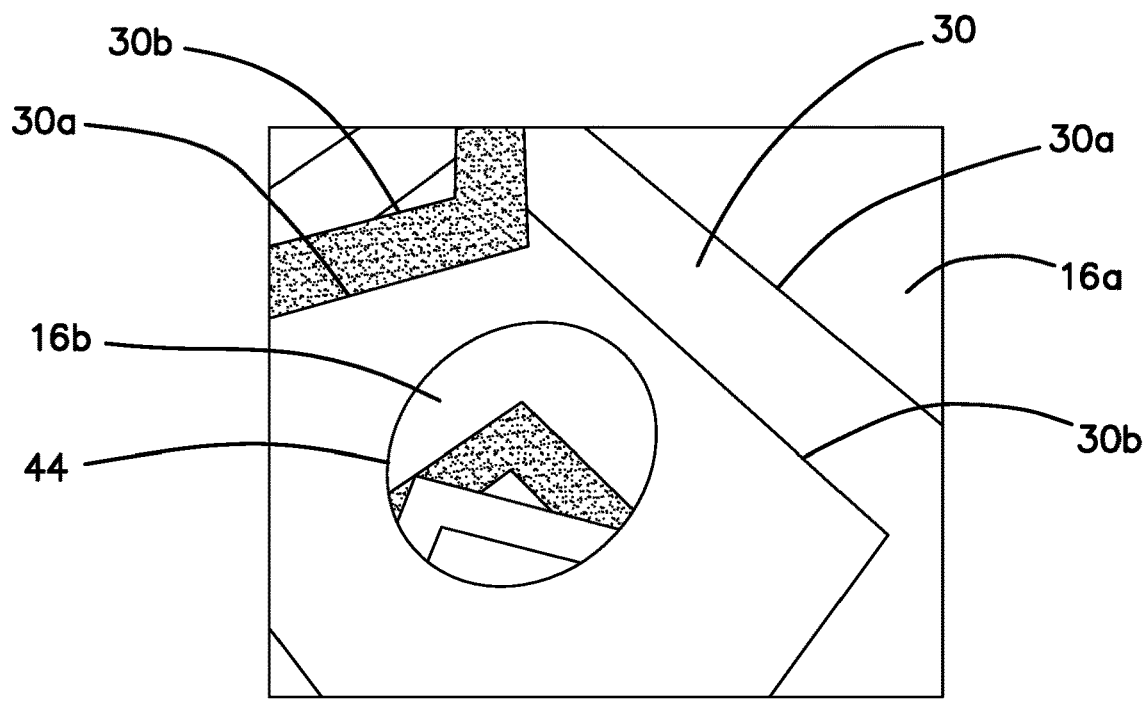
FIG. 17 is a sectional view of an insert having an opening according to the present invention.

Turning now to FIGS. 15-17, there is shown another variation of the insert 16 according to the present invention. The insert 16 is a combination of two inserts 16a, 16b stacked above each other. The insert 16 includes a first layer 16a of pre-printed targets 30 stacked in spaced-apart fashion above a second layer 16b of pre-printed targets 30. The first insert 16a is located a distance above the second insert 16b. The first insert 16a includes at least one opening 44 to provide access to the underlying second insert 16b. The at least one opening 44 is sized and configured to permit a scope to pass through the first insert 16a in order to observe the targets 30 located on the second insert 16b. The first insert 16a advantageously obscures the targets 30 on the second insert 16b, thereby, increasing the difficulty in performing the camera navigation exercises. Furthermore, as depicted in FIGS. 15-17, yet applicable to any variation described in the specification, each target 30 includes an outer border 30a defining a first target 30a and an inner border 30b defining a second target 30b. Therefore, the insert 16 advantageously provides the user additional practice variations to create a LOCK position with respect to the inner border 30b and/or outer border 30a and, thereby, practice insertion depth control. Also, the FIGS. 15-17 illustrate targets 30 of two different colors, such as a lighter yellow color and a darker blue color. The colors may be on the inner border 30b, outer border 30a, the interior of the inner border 30b or the exterior of the outer border 30b. The goal in one instruction may be to obtain LOCK positions with all of the targets 30 of the same color or to alternate between targets of different color. The color contrast between the first target 30a and the second target 30b also facilitates determination of an LOCK position for the assessor. As can be seen in FIGS. 15-17, the overlapping targets 30 are distinctly visible as a result of using different colors. More targets 30 can fit on the insert 16 in an overlapping fashion.

Figure 18:
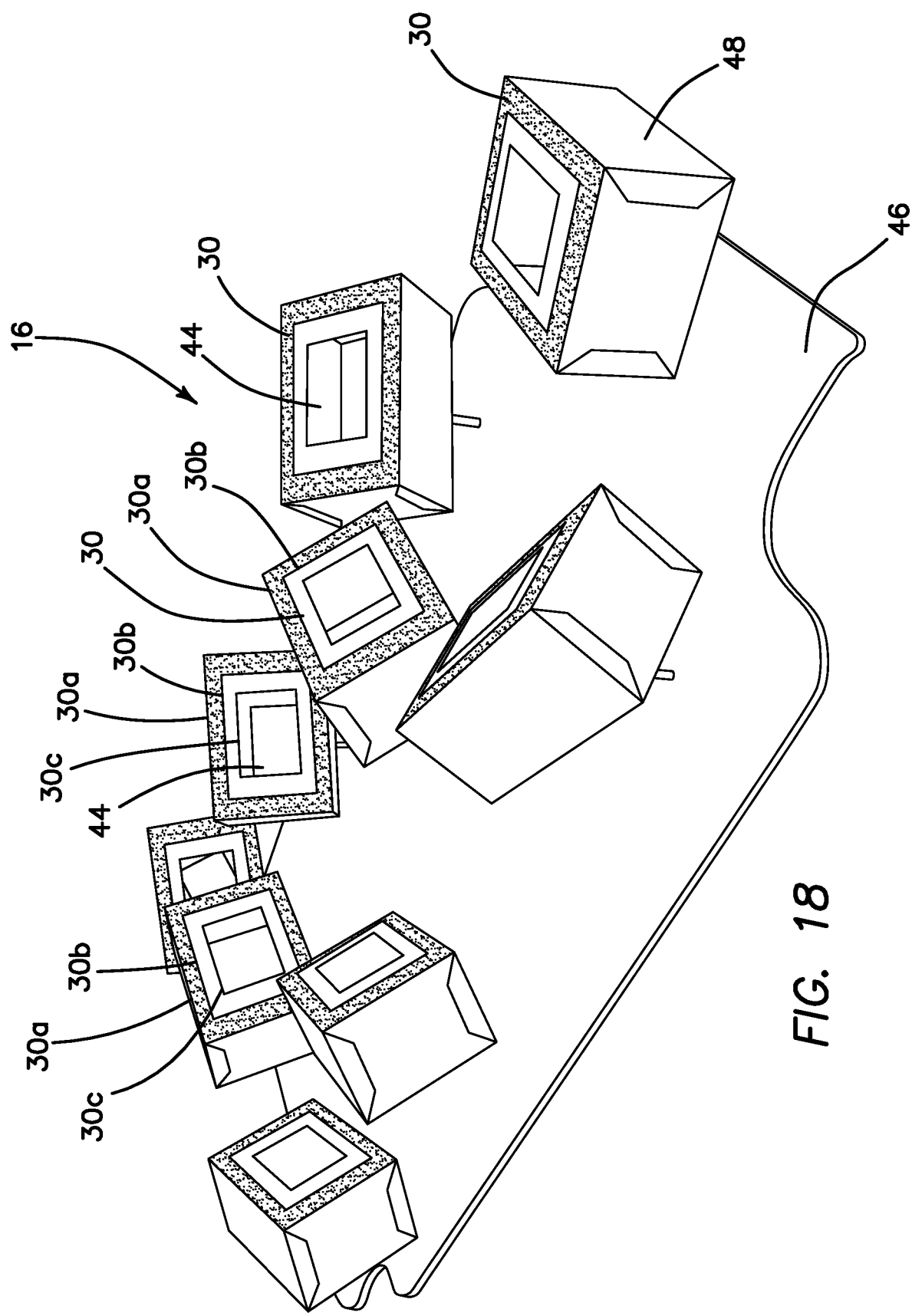
FIG. 18 is a top perspective view of an insert according to the present invention.
Figure 19:
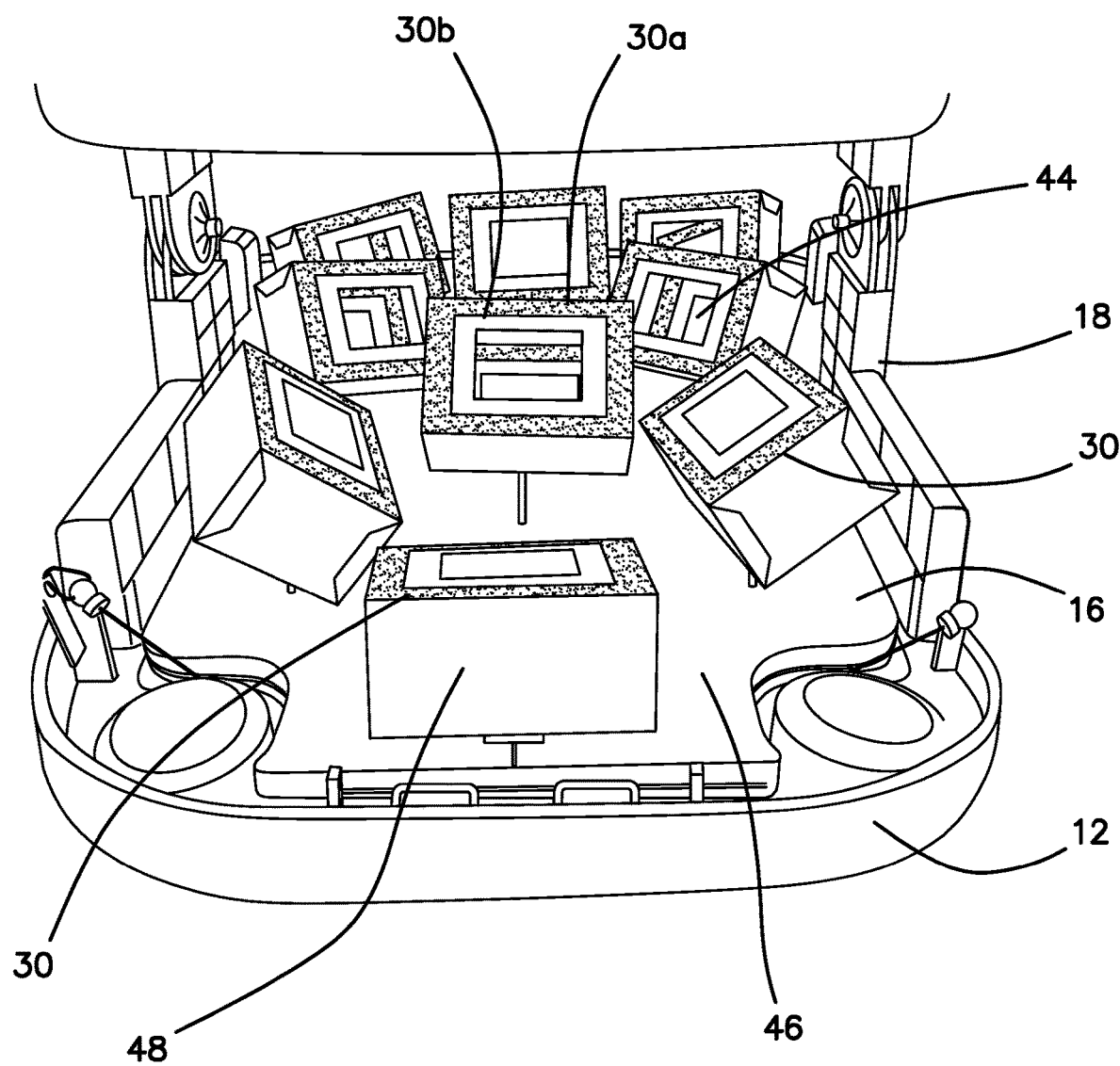
FIG. 19 is a top perspective view of an insert of FIG. 18 located on a base of a trainer according to the present invention.

Turning now to FIGS. 18-19, there is shown another variation of the insert 16 according to the present invention. In this variation, the insert 16 includes a base 46 that supports a plurality of targets 30 that are printed on at least one surface of a three-dimensional shape 48. The shape 48 is a box; however, the invention is not so limited and the shape 48 can have any suitable shape wherein at least one of the surfaces of the shape is a flat and/or quadrilateral. The shapes/boxes 48 are angulated with respect to the base 46 and, in particular, the quadrilateral/rectangular surface is angled and positioned with respect to the base 46 to achieve the desired spatial positioning to train the scope operator. In the same manner as described above, the scope operator will manipulate the scope 14 such that the rectangular target 30 viewed on the display is aligned with the frame of the display to achieve a LOCK position. One or more boxes 48 may include an opening 44 sized and configured to provide access for the scope 14 to pass through the opening 44 and view at least one additional target 30c printed inside the box 48. The outside of the box 48 may be provided with concentric targets 30a, 30b wherein a first target 30a is defined by an outer border and a second target 30b is defined by an inner border. Concentric targets may also be provided on an inner surface inside the box 48. The targets may include colors as discussed above. The dimensions of the target are designed so that they match the aspect ratio of the camera and image as seen on the trainer screen. Thus when the scope is pointed at a box, and is inserted to the correct depth, and the roll angle of the laparoscope is correct, the colored border of the box will align with the edges of the trainer display. To further provide for training on changing camera depth, one or more boxes 48 may be provided with an opening 44. The opening 44 is shown in the figures to be on the same side of the box 48 with the outer targets 30; however, the invention is not so limited and the opening can be provided on any of the sides of the three dimensional shape. One or more interior target 30c is provided that is accessible via the opening 44. The interior targets 30c can be arranged to require the user to change the camera roll angle and insertion depth relative to one or more targets 30a, 30c on the outside of the box 48. This arrangement leads users to adjust the camera insertion depth in addition to camera roll angle in order to bring the interior target 30c into the correct LOCK position/orientation. Additionally, the interior targets 30c can be designed to specifically work with an angled scope wherein targets 30c can be located on the sidewalls of the box and not just only on the back/bottom wall. By assigning a specific numbered sequence to the targets 30, a specific motion pathway for the user is defined. The level of difficulty is increased by the interior targets that require scope manipulation substantially within the confines of the box. Assessment may be automated, such as by detecting the quality of alignment of the target and providing feedback to the user such as by the frame of the display lighting up with significant colors.

Each target 30 corresponds to a specific and unique camera position that is defined by four variables. The four variables that define the camera position include (1) insertion depth, (2) roll angle, (3) polar radius, and (4) polar angle. Furthermore, the plurality of targets is arranged in a sequence of consecutive targets wherein the sequence is marked with letters or numbers. By providing an insert having an arrangement or a collection of a plurality of targets that are based on the aforementioned four variables, and assigning the created targets a specific sequence, a unique and specific motion pathway is created for the user to navigate with the scope camera. This motion pathway can be designed to mimic clinically relevant camera motions of varying complexity and difficulty. The exercise can be tailored to a particular skill level for general practice, or to a particular surgical procedure for more specific practice.

The camera navigation skills training insert of the present invention is an effective tool for teaching new surgeons how to navigate a laparoscope or other camera within a patient. The user can practice moving the camera to place the targets in view of the monitor in such a manner that is objectively assessable as to the proper positioning for each target as well as the proper sequencing of targets and speed at which proper positioning is achieved and the specified targets sequentially completed. The camera navigation skills platform is a simple, passive exercise that allows users to practice camera navigation skills without computer simulation, and that could also be used by an instructor to assess user progress and competency easily and quickly. For example, if the user can navigate successfully through the sequence of targets within a given time limit, proficiency is demonstrated.

The insert encodes a specific set of camera movements into a visual two-dimensional medium. Each target captures the four defining variables of camera position (insertion depth, roll angle, polar radius, polar angle) so that there is one unique set of these variables that will bring the target border in line with the edges of the trainer screen. A specific set of targets is then defined in such a way that the movement from each specific target to the next captures a desired movement that has clinical training or educational relevance. The alignment of the edges of targets with the edges of the trainer screen gives an instructor a clear visual indication that a specific camera orientation has been reached. The exercise is considered passive because there is no active electronic evaluation system/software, computer simulation, virtual reality to indicate the success of scope placement.

In the method, a laparoscopic trainer 12 having a video monitor 36 connected to a laparoscope 14 is provided. The laparoscope 14 is directed at an insert 16 located inside a cavity 18 of the trainer 12. An image of at least a portion of the insert 16 is captured by the laparoscope 14 and displayed on the video monitor 36. The insert 16 includes a plurality of targets 30 arranged on the insert 16 that are visible in the image on the video display 38. The positioning of the laparoscope in the three-dimensional space of the cavity with respect to the insert 16 will create the specific image on the video display 38. When the laparoscope 14 is moved in the three-dimensional space of the cavity 18, the two-dimensional image will change. One of the plurality of targets 30 is selected by the user and the laparoscope 14 is moved in the three-dimensional space of the cavity 18 until the selected target 30 appears to fill the video display 38 such that the perimeter of the selected target 30 is aligned with respect to one or more marker connected to the video monitor 36. The marker can be the perimeter/frame of the display 38 of the video monitor 36 or at least one side of the perimeter/frame of the display screen. The positioning of the laparoscope 14 is such that the selected target 30 is in alignment with one or more marker/perimeter/frame. In particular, at least one of the sides of the target 30 is aligned with at least one of the sides of the marker or all of the sides of the target 30 are aligned with all of the sides of the marker/perimeter/frame.

The insert 16 uses a series of targets 30 to guide the user through a specific sequence of motions with the camera in order to train camera navigation skills. The camera is inserted through a port 20 on a laparoscopic trainer 12 and the targets 30 are positioned on an insert 16 that fits within the trainer 12.

In one variation, the targets 30 in question are quadrilaterals/trapezoids that, when viewed from the correct orientation with the laparoscope, will perfectly align with the edges of the screen of the trainer. The motions from one target to another can include any one or more of changing the insertion depth, changing the polar angle, changing the polar radius, and changing the roll angle of the laparoscope camera.

In one variation, one or more target 30 is provided on a flat substrate material. The one or more target 30 is printed or adhered onto the substrate. In another variation, the substrate includes a plurality of surfaces arranged/angled with respect to each other such as shown in FIGS. 15-19. Complexity can be increased by changing the shape of the substrate to include more surfaces or to include cavities that require the user to look around corners or surfaces using a standard zero degree or angled scope.

In one variation, the motion path is predetermined by the sequential layout of targets on the substrate. The particular sequence is made known to the user by placing numbers, symbols, letters and the like on the targets or using colors or connecting the targets with lines drawn on the insert. In practicing, the user is required to follow the predetermined motion pathway in order to successfully complete the exercise. A plurality of locations along the desired motion pathway is selected and a unique target is provided at each location. For each location along the motion pathway, a unique target is constructed. The sequential movement through the targets then captures the original design intent with regards to the conceptual motion pathway for a particular clinical/educational goal or outcome.

By creating targets 30 and arranging them in such a manner that demands a specific camera orientation for the target border to align with at least one of the edges of the trainer screen, motion pathways from target to target that the user follows can be explicitly designed. Since the targets 30 are defined by four parameters that can also be used to explicitly define a particular camera orientation, the movement from one target to another explicitly defines a particular motion pathway for the camera. These movements can include changes to any of the four variables and/or combination of the four defining variables of camera orientation. In other words, each target represents the embodiment of a fully-defined, unique camera orientation. A motion pathway can then be fully defined by a set of fully defined camera orientations which have been encoded into a series of corresponding targets.

The visual indication of the target edges aligning with the screen edges defines a HIT which is a successful camera navigation event. Time elapses until a HIT is achieved by the user and can be measure and scored for evaluation purposes. The visual HIT gives an instructor a basis for making assessments of a user's progress and competency. Also, the HIT provides the user with a defined navigation goal. Previous to the present invention, there was no objective assessment marker for camera navigation skills training. Whereas individuals are able to navigate a camera in "freestyle" using organ models, live patients, cadavers etc., there is no objective way to measure and assess performance of camera navigation. In contrast, the present invention, when used for assessment, relies on the judgment of the instructor to determine when the target borders have been adequately aligned with the edge of the screen. The skills insert and exercise according to the present invention is designed to facilitate the objective assessment of various learning requirements of camera navigation, including the ability to maintain or adjust camera orientation, appropriate insertion depth, navigation through a sequence, etc.

Figure 20:
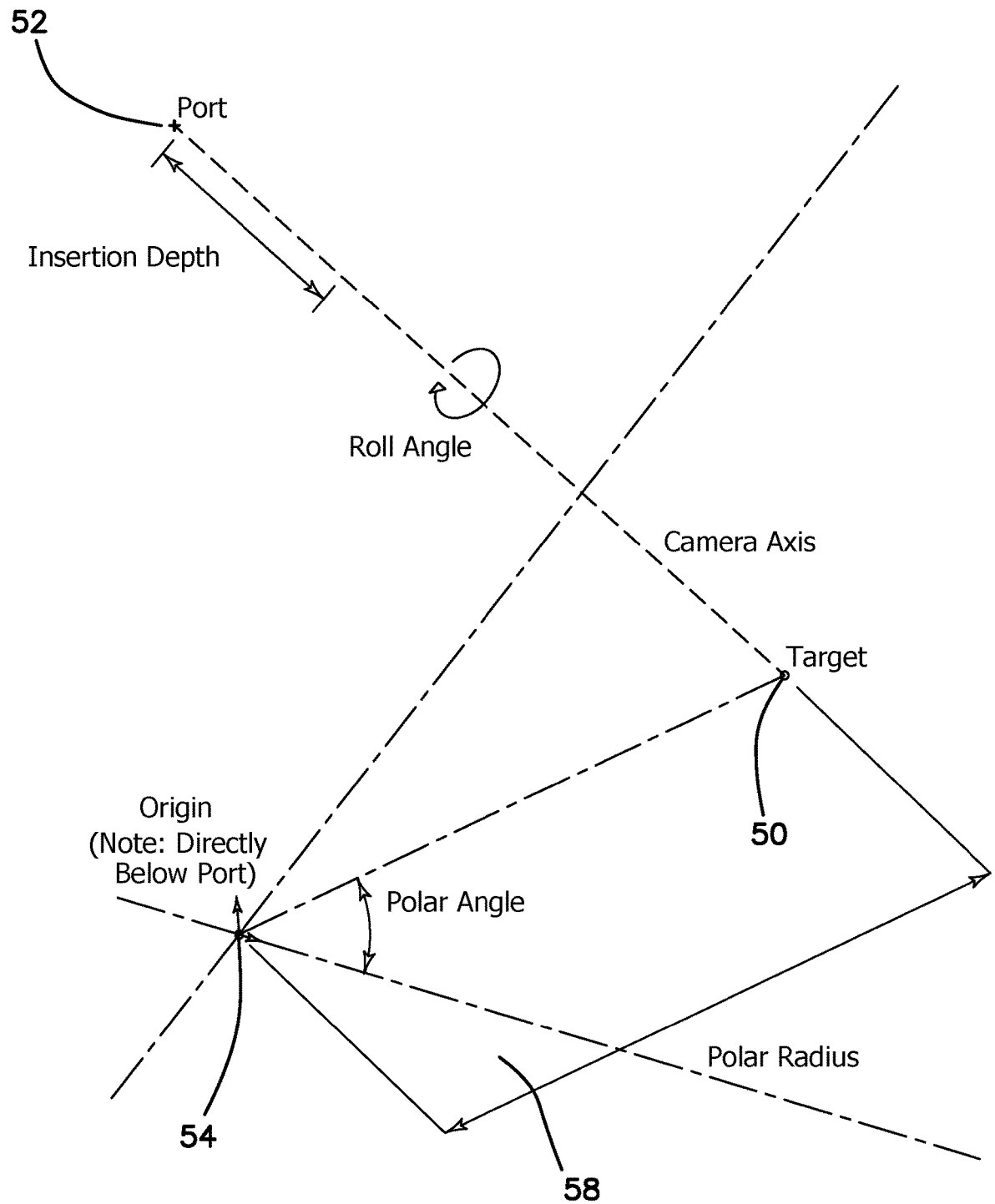
FIG. 20 is a schematic of the port, target and origin illustrating the insertion depth, roll angle, scope axis, polar angle and polar radius on a polar coordinate grid of a system according to the present invention.

Turning now to FIG. 20, a schematic of the four input variables are illustrated. FIG. 20 shows the port point 52 through which a laparoscope is inserted and a target point 50 on the insert 16 along with the four variables—insertion depth, roll angle, polar radius, polar angle—which are used in the camera navigation exercise of the present invention to define a specific camera orientation. Targets 30 are constructed based on this geometry. The target point 50 may be any point on the planar insert 16 or may be a clinically relevant point that has anatomical/surgical significance. Organs may be mapped onto the planar insert and a particular target point 50 may correspond with the location of the liver, for example. The target point 50 in the figures is the center of the ultimate target 30 that will be drawn on the insert 16. The origin 54 of the polar coordinate system used for the polar angle and polar radius is also shown. If Cartesian coordinates are employed, the same origin 54 may be used. The origin 54 is typically located in the plane 58 of the insert 16. In one variation, the origin 54 is located directly beneath the port point 52.

Figure 21:
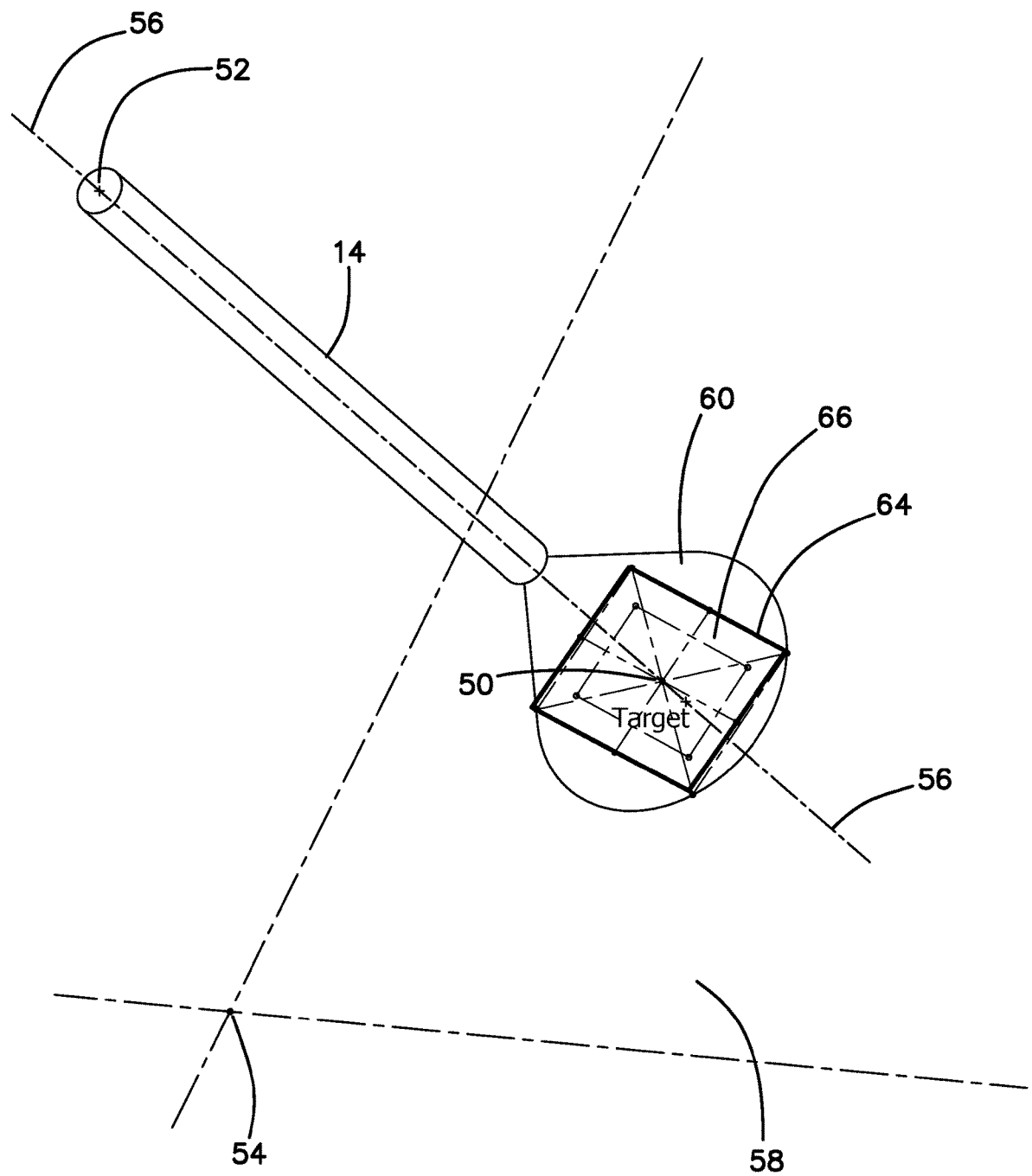
FIG. 21 is a schematic of a scope, angle of view and target point on a polar coordinate grid of a system according to the present invention.

Turning now to FIG. 21, there is shown a laparoscope 14 inserted at the port point 52. The laparoscope 14 includes a longitudinal scope axis 56. The port point 52 is fixed with respect to the insert located below the port point 52 giving the laparoscope four degrees of freedom of motion. In particular, if the insert 16 defines an X-Y plane with the Z axis perpendicular, the laparoscope 14 has a rotational envelope that includes tilting side-to-side on the X-axis and tilting forward and backward on the Y-axis to define a conical workspace having two degrees of freedom of motion with the port point 52 acting as a fulcrum point. The third degree of motion is translation of the scope up and down along the Z-axis as provided by translating the scope along its longitudinal axis through the insertion/port point 52. The fourth degree of freedom of motion is rotation of the scope about its longitudinal axis such as turning the scope left and right on the Z-axis. The laparoscope is restricted from moving left and right on the X-axis and also restricted from moving forward and backward on the Y-axis because the port point is fixed. That is the port point 52 does not move and, hence, the scope at the fulcrum does not move.

Figure 22:
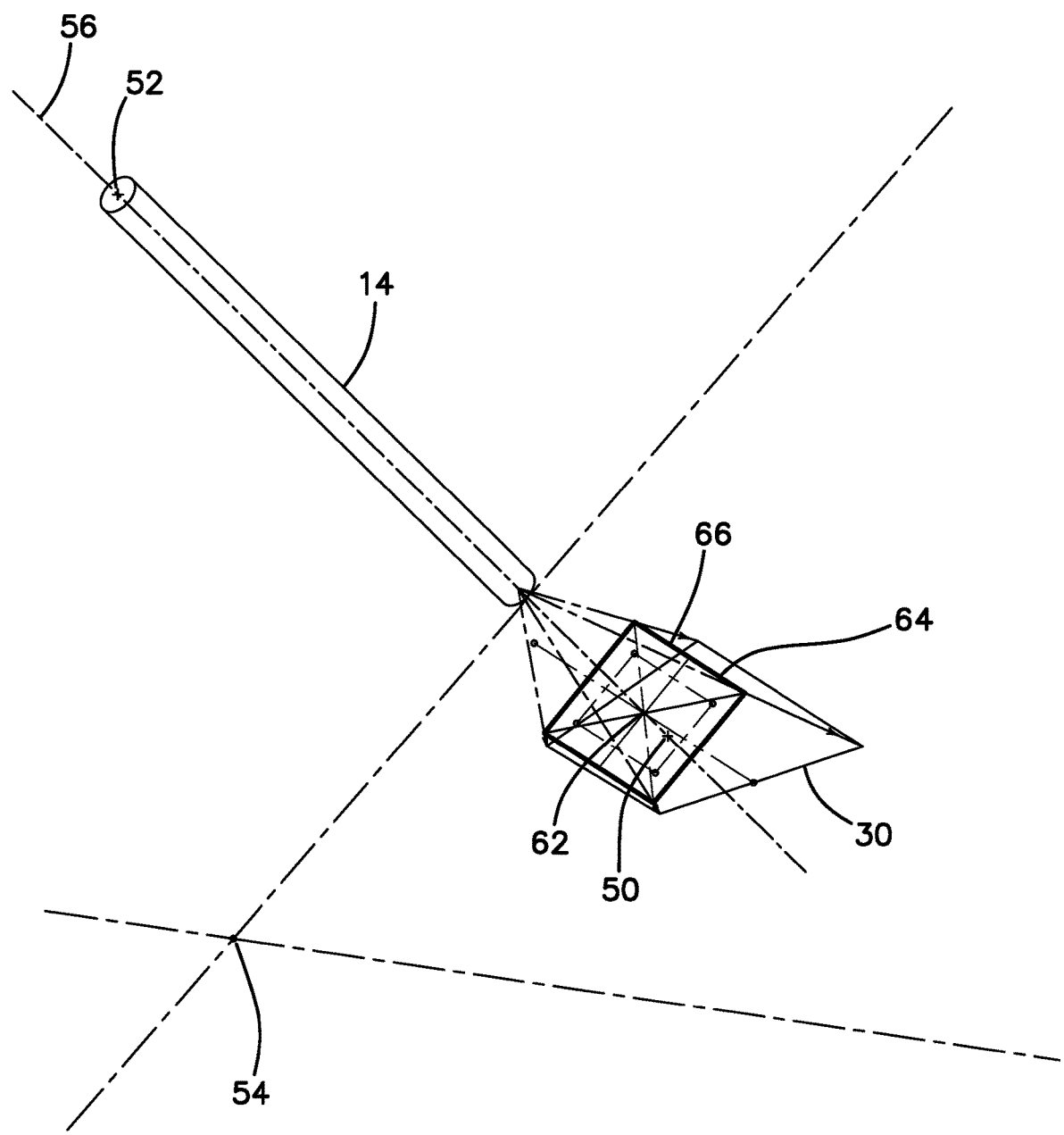
FIG. 22 is a schematic of a scope and target point on a polar coordinate grid of a system according to the present invention.
Figure 23:
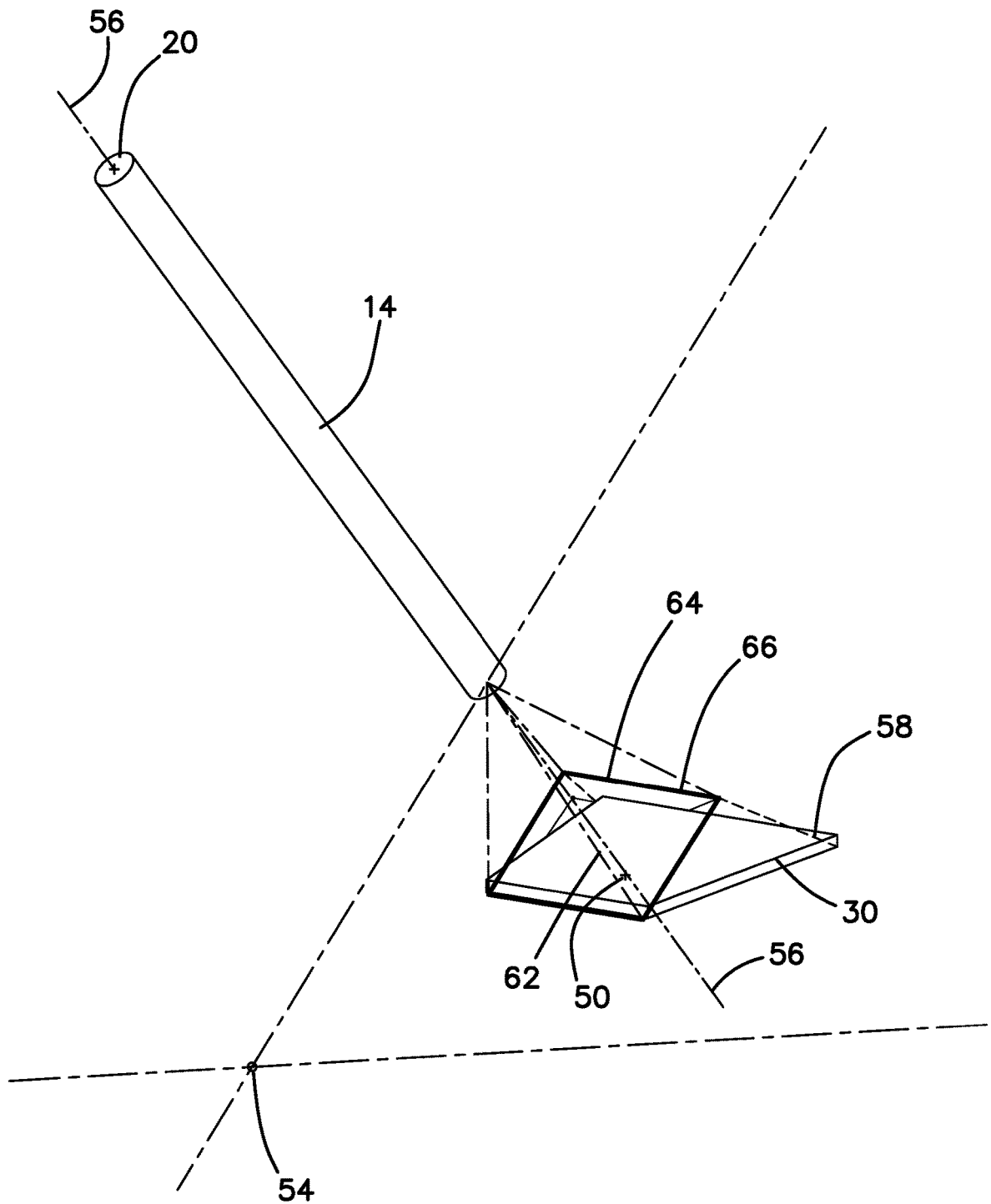
FIG. 23 is a schematic of a scope and target point on a polar coordinate grid of a system according to the present invention.

In FIG. 21, the laparoscope 14 is directed at the target point 50 such that the target point 50 is a point on the scope axis 56. The field of view is depicted by a cone 60. The ultimate target 30 that is printed on the insert 16 is a two-dimensional representation of a particular laparoscope camera orientation in which the target point 50 is on the scope axis 56. The particular laparoscope camera orientation corresponds to a virtual target point 62 that lies in a plane 64 that is perpendicular to the scope axis 56 as can be seen in FIGS. 21-23. The virtual target point 62 may correspond to a point on a virtual object above the insert plane 58. For example, the virtual object could be a gallbladder with the virtual target point 62 being the center of the gallbladder and the plane 64 perpendicular to the scope axis 56 being the most optimum viewing plane from a surgical perspective. The insertion depth is defined by moving the scope 14 along the scope axis 56. In some cases, the camera operator may have to pull the scope 14 proximally so that the distal end of the scope captures a larger field of view for exploration or room for instrumentation. Hence, the target point 50 and the insertion depth are defined with clinical purpose or to provide variety in the training exercises. The virtual plane shape 64 has a defined perimeter 66 or boundary 66 that corresponds to the aspect ratio of the camera sensor. The camera aspect ratio may be the same as the aspect ratio of the video monitor 36 but sometimes it is not. If the aspect ratio is different, the aspect ratio of the monitor 36 is used to define the boundary/perimeter 66. The plane 64 that is perpendicular to the scope axis 56 and, in particular, the boundary/perimeter 66 in the plane shape 64 that is perpendicular to the scope axis 56 has a projection onto the insert plane 58. It is this projection that defines the target 30 printed on the insert plane 58 as can be seen in FIG. 23. The projection forming the target 30 has angled perimeter lines on the insert 16 which when viewed in a LOCK position described above will have perimeter lines that are perpendicular to match the screen. A target point that is coincident with the origin will have a target 30 with perpendicular lines on the insert. In one variation, the insert plane 58 is a horizontal plane that corresponds to the base 24 of the trainer 12. The insert plane 58 may also be defined as the plane that is perpendicular to the line containing the port point 52 and origin 54. All of the targets 30 for a particular insert are then compiled into a single image, which is printed to scale and placed into the trainer with each target having one specific, fully-defined camera orientation that will bring the border of the target into alignment with the outer edge of the screen as described above. Different inserts 16 may be created/printed for use with a different insertion port 20 and port point 52 in the calculation. Also, inserts 16 may be modified to utilize other laparoscopic cameras and scopes, by reconfiguring the target design based on the camera/monitor aspect ratio.

Figure 24:
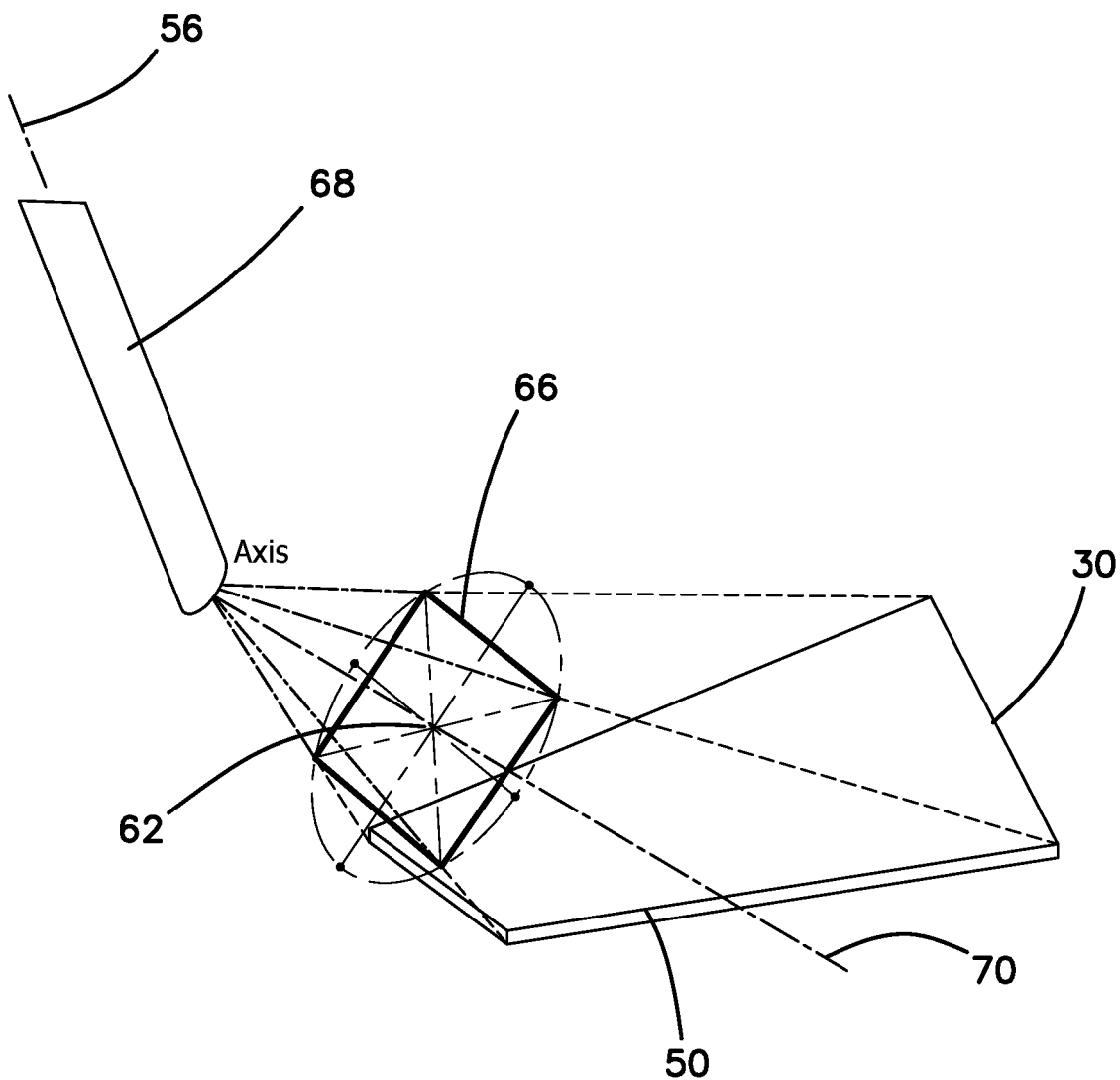
FIG. 24 is a schematic of an angled scope and target point on a polar coordinate grid of a system according to the present invention.
Figure 25A:
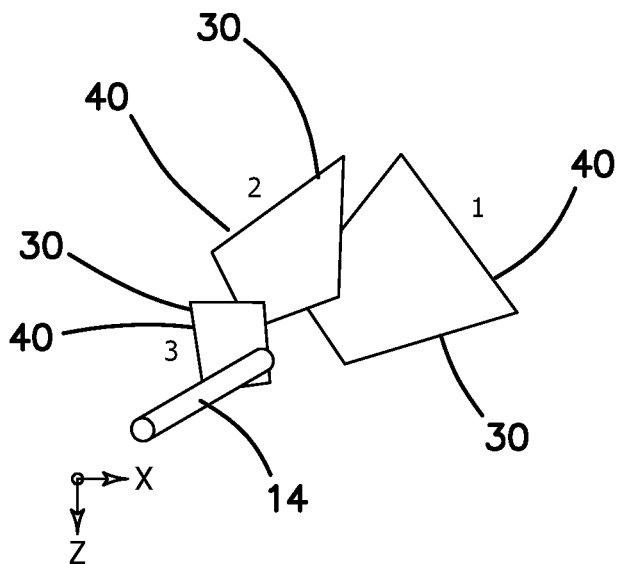
FIG. 25A is a top view schematic illustrating the effects of roll angle on target geometry using an angled degree scope according to the present invention.
Figure 25B:
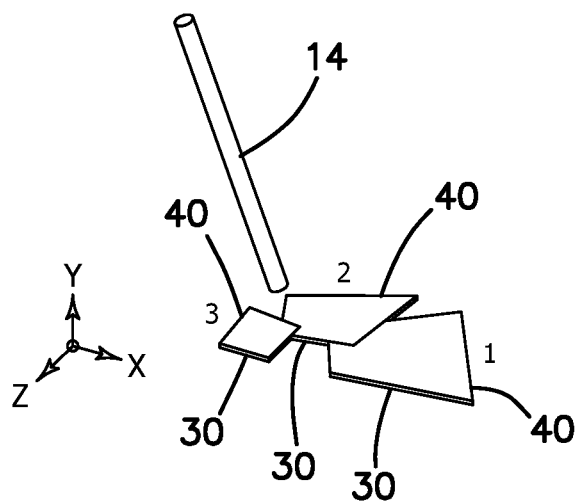
FIG. 25B is a top perspective view schematic illustrating the effects of roll angle on target geometry using an angled degree scope according to the present invention.

FIGS. 21-23 illustrate a zero degree scope 14 and FIG. 24 illustrates a schematic for an angled scope 68. The process and calculations for creating targets is the same as described for an angled scope except that instead of using the longitudinal axis 56 of the scope as in a zero angle scope 14, the angled axis 70 is used. The angled axis 70 is perpendicular to the lens plane of the angled scope 68. The same four input variables fully define the target geometry. However, the roll angle has an increased effect on the target geometry when using an angled scope as can be seen in FIG. 25. FIG. 25 shows the dramatic effect that the roll angle has on the target geometry when using an angled scope with reference to the top side 40. Inserts 16 that have openings 44 that provide access to second level targets 30c are particularly suited for use with an angled scope because they mimic conditions often encountered during surgery where the camera operator must use the angled scope to visualize anatomical structures that would be impossible to see using a zero degree scope. Therefore, the present invention also provides an effective exercise platform for practicing camera navigation with an angled scope in difficult anatomical situations.

Figure 26A:
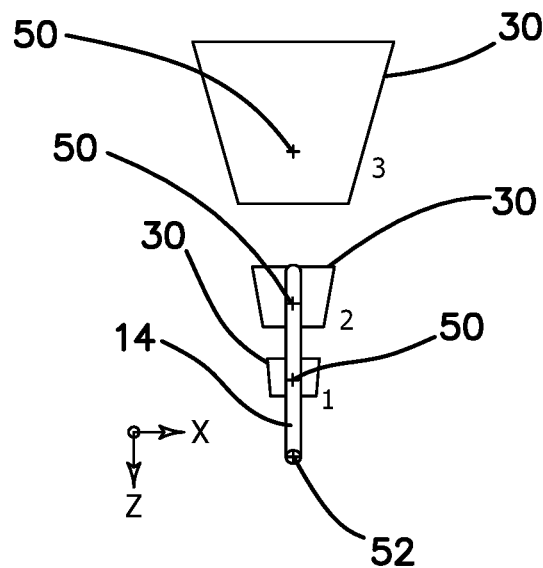
FIG. 26A is a top view schematic illustrating the effects of polar radius on target geometry using a zero degree scope according to the present invention.
Figure 26B:
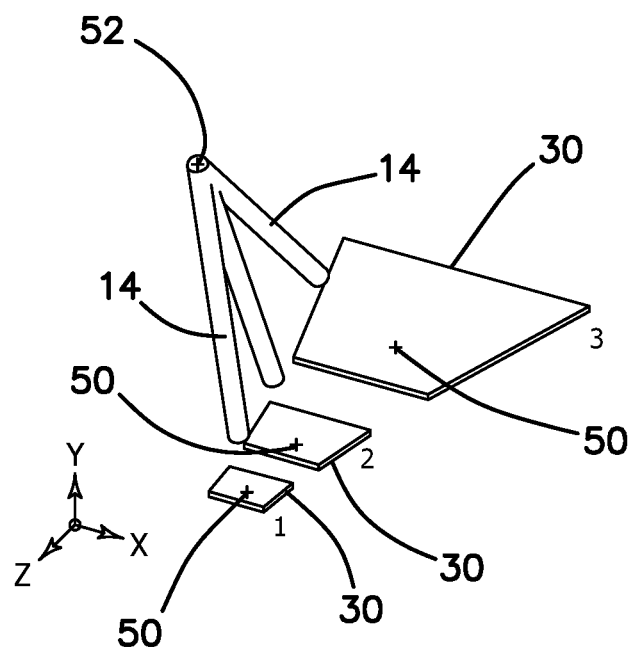
FIG. 26B is a top perspective schematic illustrating the effects of polar radius on target geometry using a zero degree scope according to the present invention.

FIG. 26 illustrates the difference between targets 30 having a different polar radius with the insertion depth, roll angle, and polar angle being constant. Because of this, these targets 30 lead the user to only change the polar radius of the scope 14 as shown in the figures.

Figure 27A:
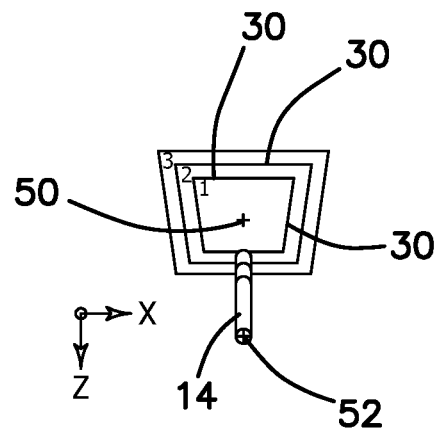
FIG. 27A is a top view schematic illustrating the effects of insertion depth on target geometry using a zero degree scope according to the present invention.
Figure 27B:
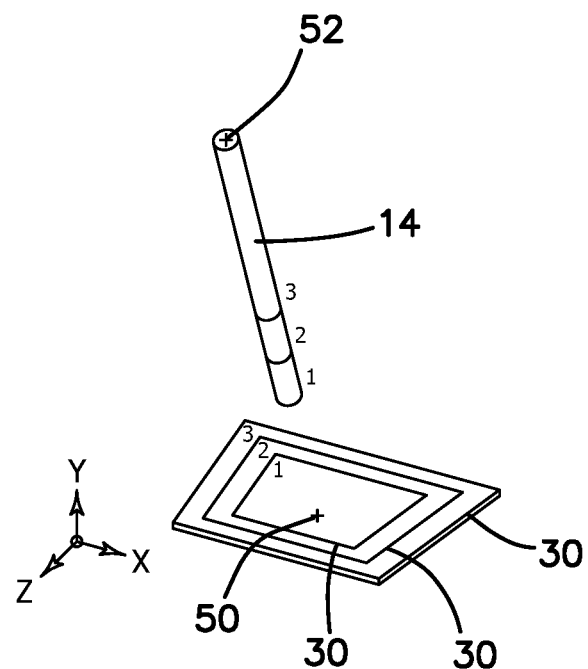
FIG. 27B is a top perspective view schematic illustrating the effects of insertion depth on target geometry using a zero degree scope according to the present invention.

FIG. 27 illustrates the difference between targets 30 having a different insertion depth with the polar radius, roll angle, and polar angle being constant. Because of this, these targets 30 lead the user to only practice changing the insertion depth of the scope 14 in going from steps 1-3 as shown in the figures.

Figure 28A:
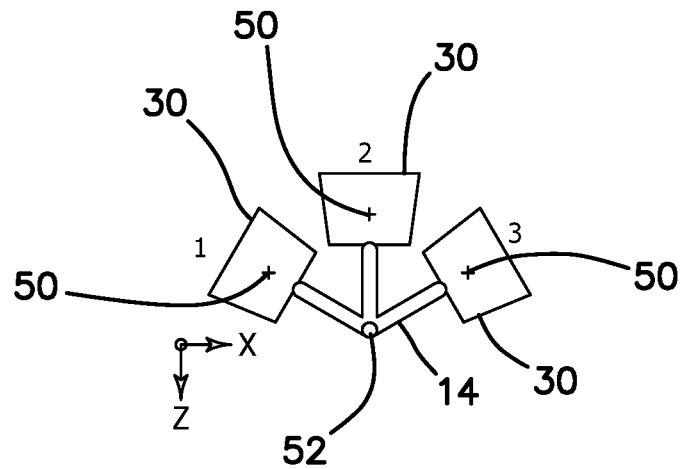
FIG. 28A is a top view schematic illustrating the effects of polar angle on target geometry using a zero degree scope according to the present invention.
Figure 28B:
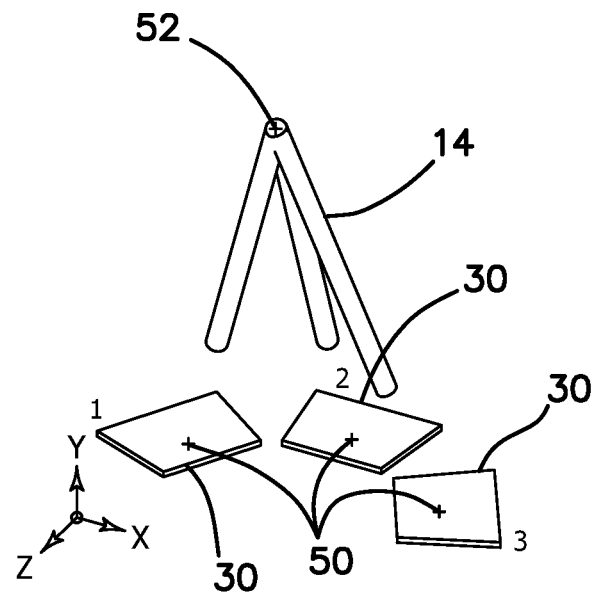
FIG. 28B is a top perspective view schematic illustrating the effects of polar angle on target geometry using a zero degree scope according to the present invention.

FIG. 28 illustrates the difference between targets 30 having a different polar angle with the insertion depth, roll angle, and polar radius being constant. Because of this, these targets 30 lead the user to only practice changing the polar angle of the scope 14 in going from steps 1-3 as shown in the figures.

Figure 29A:
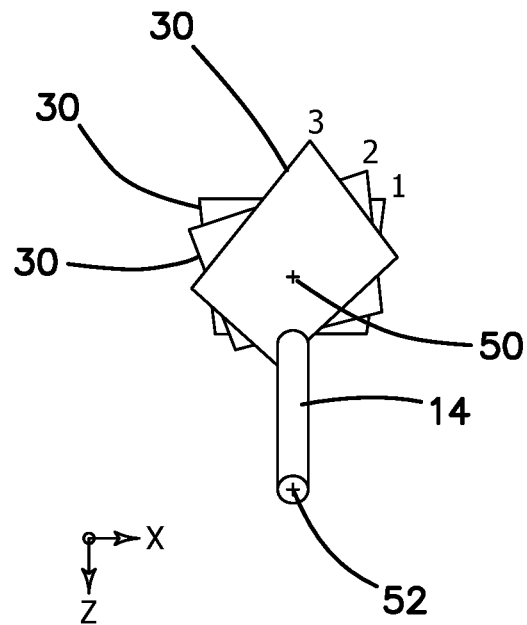
FIG. 29A is a top view schematic illustrating the effects of roll angle on target geometry using a zero degree scope according to the present invention.
Figure 29B:
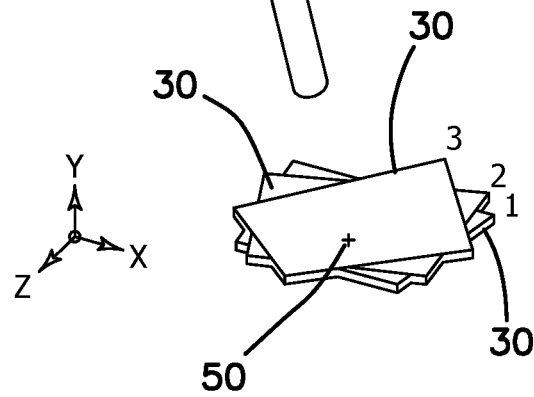
FIG. 29B is a top perspective view schematic illustrating the effects of roll angle on target geometry using a zero degree scope according to the present invention.

FIG. 29 illustrates the difference between targets 30 having a different roll angle with the insertion depth, polar radius, and polar angle being constant. Because of this, these targets 30 lead the user to only practice changing the roll angle of the scope 14 as shown in the figures.

Figure 30:
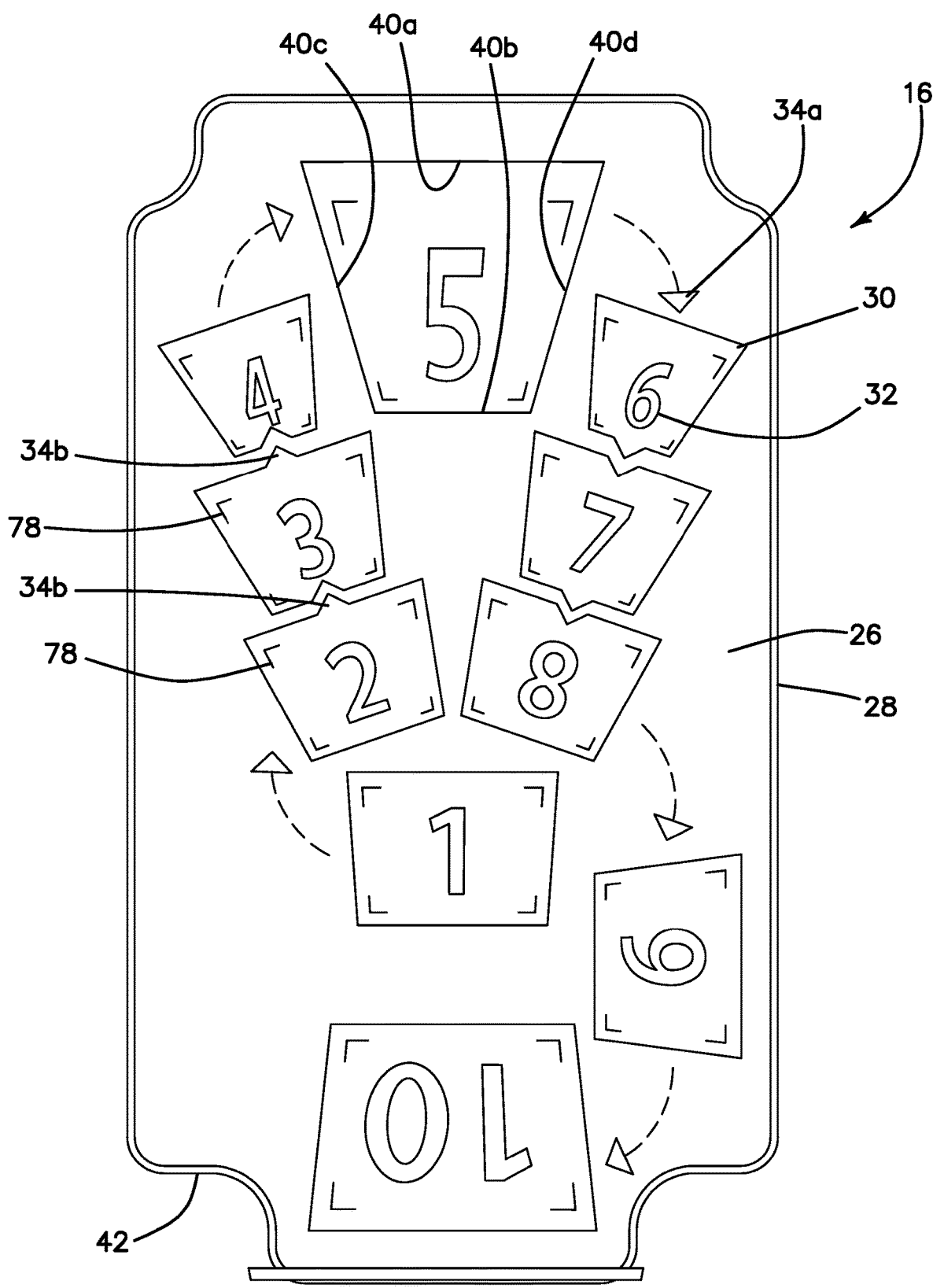
FIG. 30 is a top view of an insert according to the present invention.
Figure 31:
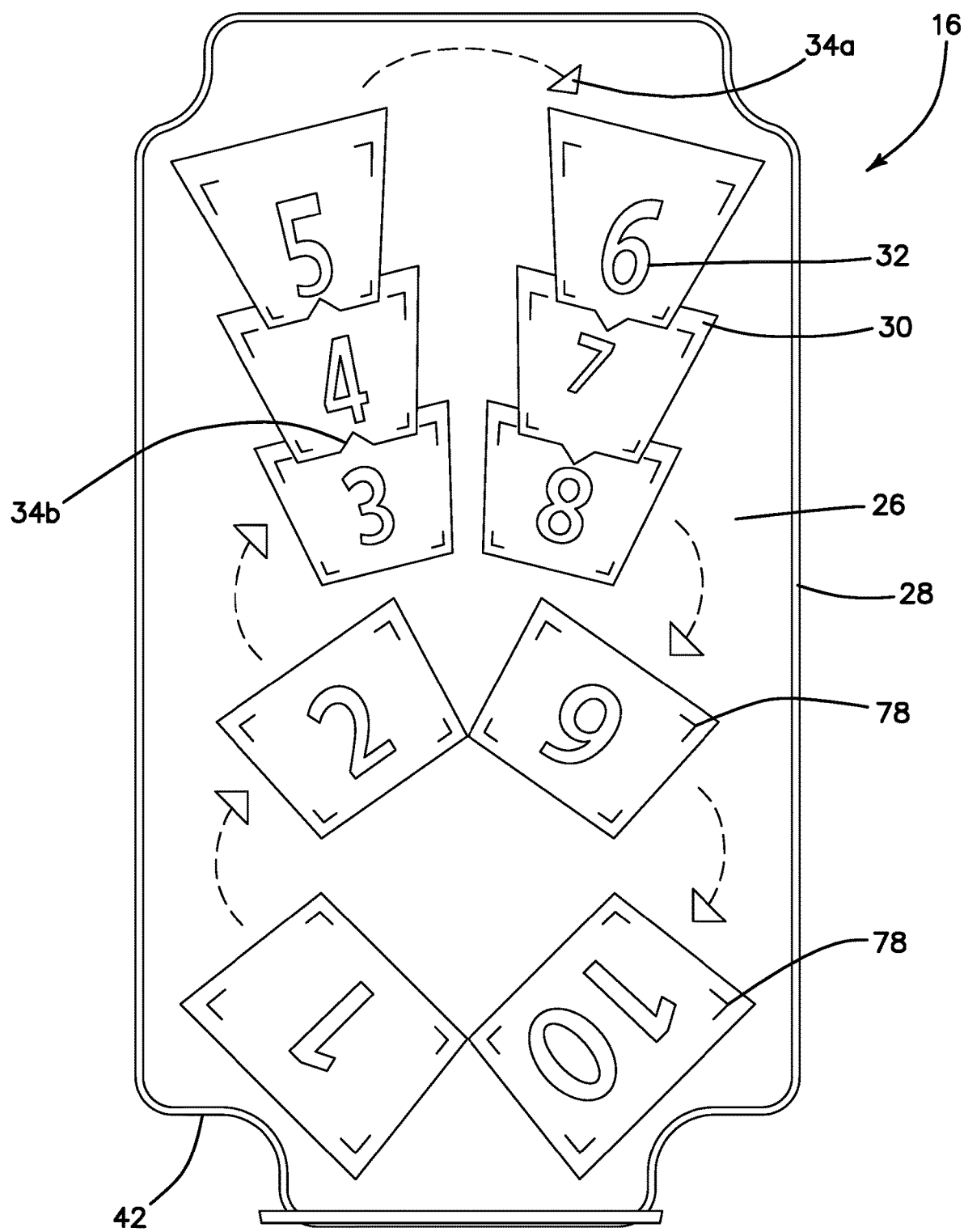
FIG. 31 is a top view of an insert according to the present invention.
Figure 32:
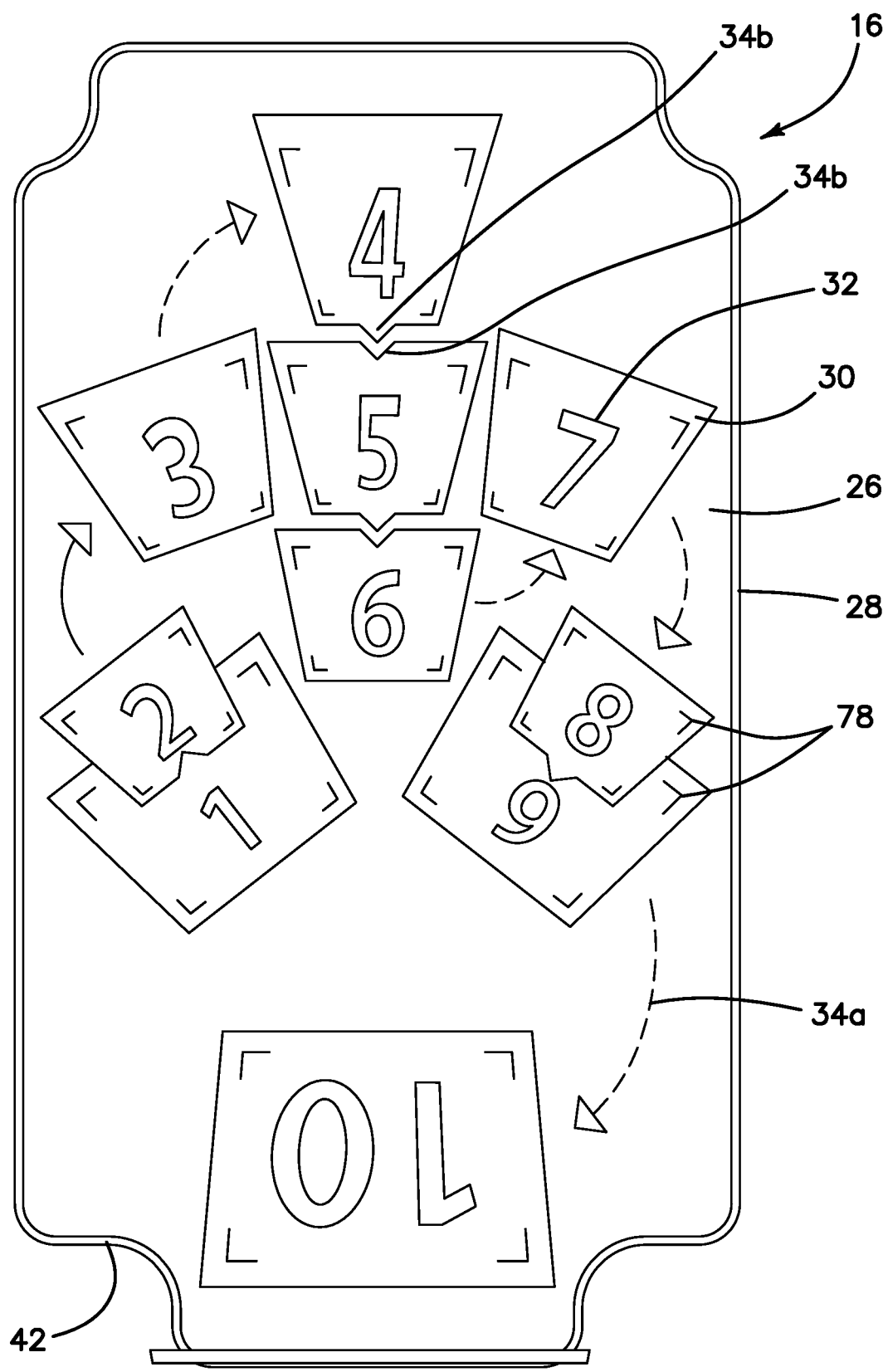
FIG. 32 is a top view of an insert according to the present invention.

Turning to FIGS. 30-32, there are shown other variations of an insert 16 according to the present invention. The insert 16 includes a flat, planar top surface 26 and an oppositely disposed bottom surface 28. The insert 16 is sized and configured to be received in the frame of the base 24 of a trainer 12. The top surface 26 of the insert 16 includes a plurality of navigation targets 30. The targets 30 are shown to be quadrilateral, in particular, trapezoids and, more in particular, isosceles trapezoids; however, the invention is not so limited and the targets may be another shape such as polygonal, circular. For example, each target 30 has at least one straight side or line interconnected by one or more curve or line.

Each target 30 includes a sequence marker 32 such as a number. The sequence marker 32 indicates the sequential order in which the targets 30 are to be brought in view of camera and aligned with the display. Taken together, the sequence of targets 30 denoted by the sequence marker 32 in combination with the size, shape and orientation of each target 30 may have clinical significance in addition to training significance. For example, the varying size of each target 30 helps the user train in-and-out camera zooming skills; whereas, the sequence of multiple targets 30 may be a pathway defined by a specific surgical procedure.

Each target 30 may also include an additional orientation marker. In FIGS. 30-32, the number 32 located inside the target 30 serves as both a sequence indicator between multiple targets 30 as well as an orientation marker for each individual target 30. The orientation marker indicates to the user how to orientate the target 30 with respect to the screen display. For example, the user is required to orientate the number in a right-side up manner such that the number is readable and such that the number is not upside-down. Another example of an orientation marker is a line of certain significant thickness located at the bottom of the target 30 to denote which side of the target 30 is the bottom of the target 30, for example to be aligned with the bottom of the display, in order to alleviate confusion as to the proper orientation of the target 30. The orientation marker shows the orientation the user should have when focusing on an individual target.

The top surface 26 may optionally further include a direction marker 34 also called a pathway marker 34. One example of a direction marker 34a is a line and an arrow drawn on the top surface 26. The line and arrow are located between two adjacent targets 30. When the user zooms out with the camera view, the base of the arrow will become visible to the user at which point the user will know to follow to the arrow to the next target 30 in the sequence. A secondary direction marker 34b may also be provided to the user. An example of a secondary direction marker 34b is an indentation or discontinuity in the side border of a target 30. The indentation or discontinuity is in a shape of an arrow and appears as an extension extending away from a target or an arrow-like shaped indentation into the target 30. The secondary direction marker 34b provides the user with a direction to move the camera after alignment of the target 30 with the display frame. The secondary direction marker 34b provides to the user a notification of the sequence direction without zooming out too far with the camera as may be the case with a direction marker comprising an arrow located between two adjacent targets 30. The pathway/direction marker 34 also indicates the sequence of targets 30 to the user. The dashed line of the direction marker 34 also guide the rotation direction. The orientation marker 32 may also be a word, letter, symbol or picture that the user will know how to orientate right-side up within the display frame. The sequence of targets 30 may be determined with a set of ordered or random flashcards having a corresponding set of symbols, words or pictures as shown on the targets 30. The instructor may draw a card from a plurality of cards and the user would then try to locate the symbol/picture on the insert 16 with the scope by bringing the symbol/picture into view on the display. In one variation, the symbols/pictures on the targets 30 correlate to anatomy with respect to their relative location on the insert.

As described above, the user aligns one or more of the perimeter edges with the one or more perimeter edges of the frame of the display monitor. In the variation shown in FIGS. 30-32, the insert 16 includes an alignment marker 78 in addition to the perimeter/border of the target polygon. The alignment marker 78 includes one or more bracket, line or combination of lines located a distance inside from the outer edge/perimeter of the target. In particular, the bracket of FIGS. 30-32 comprises two lines intersecting to form a corner for alignment in one of the corners of a rectangular display screen. In the variation shown in FIGS. 30-32, the alignment marker 78 includes four brackets, each having a corner, for alignment with the four corners of the display screen. The secondary alignment marker 78 is in addition to the alignment marker defined by the outer perimeter/border of the target 30. This arrangement allows the user to align at least one border/perimeter of a target with the perimeter of the display screen, or align the at least one of the brackets with at least one corner of the display screen or align the space between the at least one bracket and corresponding perimeter/border corner. Since the insert 16 is intended to accommodate a variety of users with varying levels of skill and dexterity, the combination of a primary and secondary alignment markers advantageously establishes a margin of error for each skill level. For example, a novice user would be instructed to align the target border/perimeter with the frame of the display. More skilled users would be instructed to align the brackets with the frame of the display. Because the brackets are not interconnected, the user's eye must travel a longer distance or employ peripheral vision and increased awareness for quick and accurate camera navigation. A two-stage instruction may be provided to the user to first align the perimeter/border followed by the relatively more difficult zooming in to align the brackets with the display screen. In the variation of FIGS. 30-32, the user attempts to align all four brackets 78 with all four corners of the display screen.

The bottom surface 28 of the insert 16 may be provided with another pattern or arrangement of targets 30 that is different from the one on the upper surface 26 so that the insert 16 can be flipped over for a different arrangement of targets 30. In another variation, the bottom surface 28 of the insert 16 includes instructions for set-up and training with the insert 16. In the variation in which each target 30 is a quadrilateral/trapezoid, each quadrilateral/trapezoid has a top side 40a, a bottom side 40b, a left side 40c and a right side 40d. The targets 30 are configured to be used with a particular scope/camera 14. The insert 16 is placed onto the base 24 of the trainer 12 as shown in FIG. 1. The sides of the insert 16 may include to cutouts 42 to help position the insert 16 in the trainer 12. After the insert 16 is positioned on the base 24 of a trainer 12, the user is instructed to position the laparoscopic camera in the center port of the trainer. The size and shape of the targets 30 are based on a fixed camera port point 52. The user is instructed to begin with target number one and use the trainer camera/scope to align the bracket corners of each target 30 with the outer edges of the screen and to progress sequentially to the end. The brackets may be colored to make the exercise more or less difficult depending on the color contrast. For example, a brightly colored bracket may be more easily aligned relative to a bracket having less color contrast with its background.

With particular reference to FIG. 30, the configuration of targets 30 on the insert 16 is loosely based on a cholecystectomy procedure. The arrangement is focused on zooming in and out with a plurality of targets 30 dedicated to this motion. This design also guides the user to curl the camera approximately 180 degrees by including a target 30 at a 90 degree orientation.

With particular reference to FIG. 31, the configuration of targets 30 on the insert 16 is loosely based on a right colectomy in which the right colon is removed. This arrangement is difficult because the targets require the user to curl the camera and maintain a steady image at an awkward angle and is focused on teaching rotation of the camera about various axes more than zooming in and out.

With particular reference to FIG. 32, the configuration of targets 30 on this insert 16 is loosely based on a vaginal hysterectomy. This arrangement focuses on a variety of types of camera movement.

Figure 33:
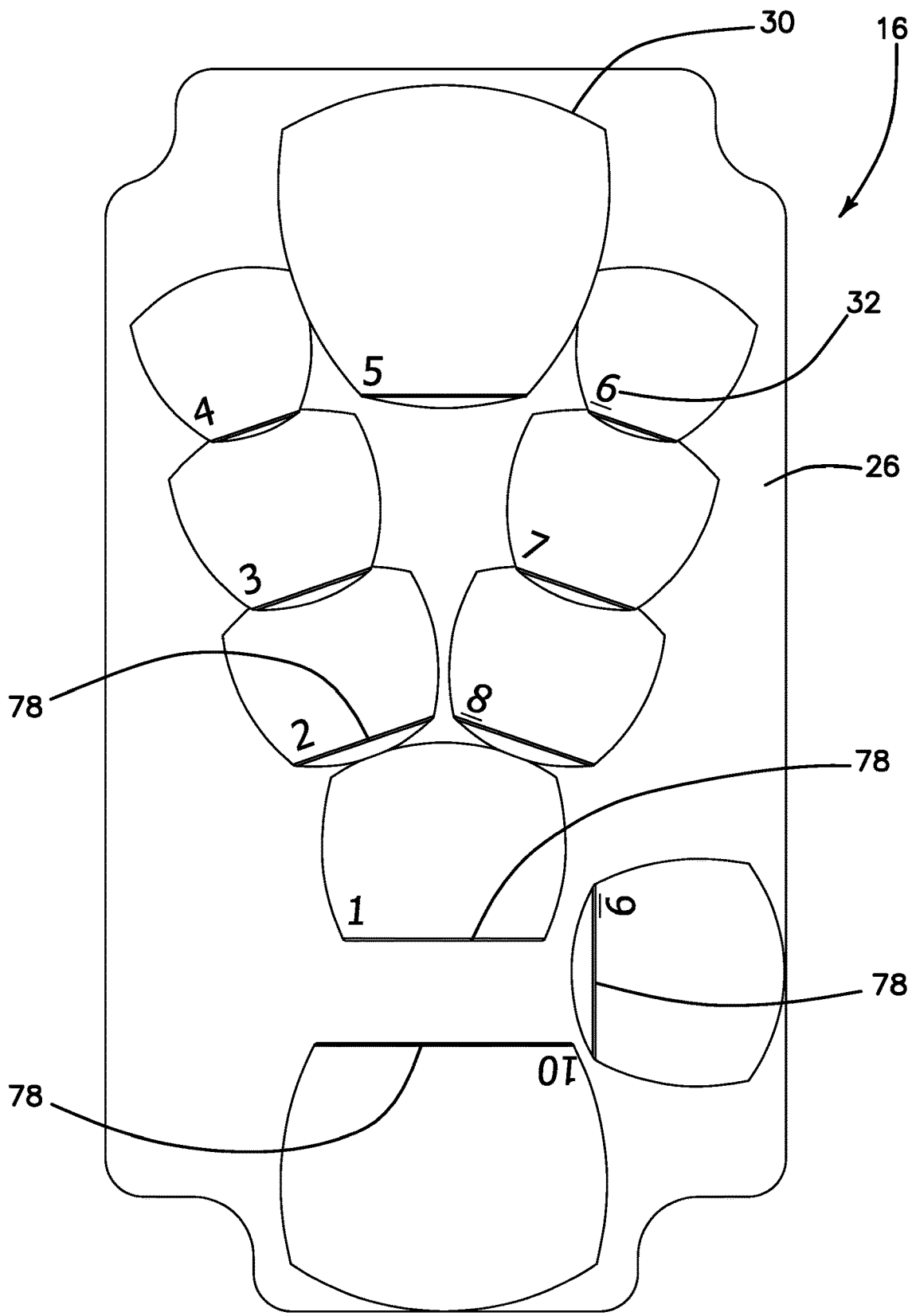
FIG. 33 is a top view of an insert according to the present invention.

Turning now to FIG. 33, there is shown another variation of an insert 16 according to the present invention. The insert 16 includes a plurality of targets 30 with each target having an alignment marker 78 comprising one straight line. The line has a length and a width thickness. The length of the line corresponds to the aspect ratio of the camera such that a HIT or LOCK is achieved when the line is aligned with one of the sides of the display screen and the length of the line extends between two parallel adjacent sides of the display screen. The user will align the two endpoints of the line with two corners, such as the bottom two corners, of the screen. A sequence marker 32 is provided in the form of a number which also serves as an orientation marker indicating to the user to orientate the number right-side-up. The line 78 is interconnected by a shape comprising curved lines such as for targets 1 and 10. For the remaining targets 30, the line 78 intersects and is encompassed by a curved shape. The shape may be colored and generally serve as an orientation marker wherein the majority of the shape is located within the display screen when the line 78 is in alignment. In one variation, the target 30 comprises only a line 78 in combination with an instruction to align the line 78 with one of the four sides of a display screen. For example, the instruction would be for the user to align all of the lines 78 of targets 30 with the bottom side of a display screen. Alternatively, a particular side of the screen that is to be aligned with the line 78 can be indicated on the target itself. Optionally, each target 30 may be provided with a sequence marker and/or an orientation marker and/or a direction marker. The line thickness is approximately 0.06 inches or between 0.04 inches and 0.08 inches or between 0.03 inches and 0.12 inches. This value gives users a small range of insertion depths and angles to place the camera and still have the line showing on the bottom of the screen. If the thickness of the line is larger or too large, the exercise becomes oversimplified and if the line thickness is too small, the exercise becomes too difficult. Of course, the line can be larger or smaller than the range provided and be within the scope of the present invention. The edges of the line are parallel to the line of orientation for each respective target so that they will line up with the bottom edge of the screen. Of course, any of the exercises may include a duration instruction for holding any one of the targets in an alignment LOCK or HIT position.

The design, geometry, placement and sequence of targets 30 on the insert 16 encode the various learning requirements identified as being critical to the development of proficiency in camera navigation. The geometry of shapes on the camera navigation exercise, in consideration of polar coordinates, insertion depth, and roll, facilitate the assessment of camera navigation skills. The user has a defined objective to "fill the screen" and through deliberate practice, the user is able to perform this task with increasing proficiency. The structure of the insert and exercise associated with the targets advantageously adds value by creating a standard objective assessment that is consistent for all learners as opposed to varying degrees of feedback on one's competency level from multiple surgeons/evaluators. The system enables the practice of basic camera navigation skills such as hand-eye coordination, visual-spatial cognition, and dexterity in a non-virtual setting without computer simulations, video projections and the like. The assessor is advantageously provided with a way to assess a user's success objectively and also with consistency across assessments and consistency across different assessors. Because the alignment in a HIT or LOCK positioning is very precise and perhaps more precise than needed, the system advantageously forces greater accuracy in the learner. For example, alignment of the screen with an inner target 30*b* or outer target 30*a* or at a location between the inner target 30*b* and outer target 30*a*, as shown in FIGS. 15-19, requires more precision than merely bringing a target point 50 generally in view on the screen as would be the case with any other camera navigation training system employing, for example, model organs and the like. The system provides a way to assess camera navigation skills. Skills development can be encoded in sequential target progression per insert as well as across a set of inserts having progressively difficult or different skill levels or skills encoded. Furthermore, the system is reusable and easily portable.

It is understood that various modifications may be made to the embodiments disclosed herein. Therefore, the above description should not be construed as limiting, but merely as exemplifications of preferred embodiments. Those skilled in the art will envision other modifications within the scope and spirit of the present disclosure.

I claim:

1. A system for training surgical camera navigation with a surgical scope, the system comprising:
   a surgical scope;
   a video display screen operably connected to the surgical scope; and
   a box trainer having a planar base and a top, wherein the top is spaced apart from the planar base to define a cavity that is configured to receive an interchangeable insert; and
   the interchangeable insert having a flat surface, wherein the interchangeable insert comprises a plurality of two-dimensional targets on an upper surface of the interchangeable insert having a first pre-determined shape that is captured via the surgical scope and displayed on the video display screen, wherein the plurality of two-dimensional targets are configured to guide a user to manipulate the surgical scope to different positions and different orientations above a particular two-dimensional target within the cavity, and wherein the first pre-determined shape displayed on the video display screen of one of the plurality of two-dimensional targets changes to a second pre-determined shape displayed on the video display screen when the surgical scope is manipulated to a pre-determined location and having a pre-determined orientation for that one of the plurality of two-dimensional target.

2. The system of claim 1, wherein the surgical scope further comprises a camera sensor.

3. The system of claim 1, wherein the top has one or more ports for insertion of the surgical scope to access the interchangeable insert housed within the cavity of the box trainer.

4. The system of claim 1, wherein the plurality of two-dimensional targets are printed onto the upper surface of the interchangeable insert.

5. The system of claim 1, wherein the first pre-determined shape is quadrilateral.

6. The system of claim 1, wherein the first pre-determined shape is trapezoidal.

7. The system of claim 6, wherein the second pre-determined shape is rectangular.

8. The system of claim 1, wherein each of the plurality of two-dimensional targets further comprises a marking that individually denotes a bottom of each of the plurality of two-dimensional targets.

9. The system of claim 1, wherein the interchangeable insert further comprises markings that denotes a path or sequence for two or more of the plurality of two-dimensional targets.

10. The system of claim 1, wherein the interchangeable insert comprises two layers each having their respective plurality of two-dimensional targets, wherein a first layer is stacked in a spaced-apart fashion above a second layer and obscures the plurality of two-dimensional targets associated with the second layer, and wherein the first layer includes at least one opening to provide access to the second layer.

11. A surgical camera navigation insert comprising:
a flat planar upper surface;
a plurality of two-dimensional targets printed on the flat planar upper surface, each of the plurality of two-dimensional targets having a trapezoidal shape and a plurality of alignment markers with at least one of the plurality of alignment markers placed at a corner of each of the plurality of two-dimensional targets;
a plurality of direction markers printed on the flat planar upper surface with each of the plurality of direction markers disposed between two different two-dimensional targets of the plurality of two-dimensional targets; and
a plurality of secondary direction markers, wherein at least one of the plurality of secondary direction markers is a discontinuity in a side border of one or more of the plurality of two-dimensional targets.

12. The insert of claim 11, wherein the insert comprises two layers each having their respective plurality of two-dimensional targets, wherein a first layer is stacked in a spaced-apart fashion above a second layer and obscures the plurality of two-dimensional targets associated with the second layer, and wherein the first layer includes at least one opening to provide access to the second layer.

13. The insert of claim 11, wherein the discontinuity in the side border of one or more of the plurality of two-dimensional targets comprises an arrow shaped extension extending away from of the one or more of the plurality of two-dimensional targets.

14. The insert of claim 11, wherein at least one of the plurality of secondary direction markers is an arrow shaped indentation in a side border of one or more of the plurality of two-dimensional targets.

15. The insert of claim 11, further comprising a bottom surface and a plurality of two-dimensional targets printed on the bottom surface.

16. The insert of claim 15, wherein the plurality of two-dimensional targets printed on the flat planar upper surface are arranged in a first pattern and the plurality of two-dimensional targets printed on the bottom surface are arranged in a second pattern being different from the first pattern.

17. The insert of claim 11, wherein each of the plurality of two-dimensional targets further comprises a marking individually denoting a bottom for each of the plurality of two-dimensional target.

18. The insert of claim 11, further comprising a transparent layer with removable markings.

19. The insert of claim 11, wherein the plurality of alignment markers are placed at each corner of each of the plurality of two-dimensional targets.

* * * * *